(12) United States Patent
Hwang et al.

(10) Patent No.: US 7,786,200 B2
(45) Date of Patent: Aug. 31, 2010

(54) SULFUR-CONTAINING SILANE, FILLED ELASTOMERIC COMPOSITIONS CONTAINING SAME AND ARTICLES MADE THEREFROM

(75) Inventors: Lesley Hwang, Chappaqua, NY (US); Antonio Chaves, Chappaqua, NY (US); Eric R. Pohl, Mt. Kisco, NY (US)

(73) Assignee: Momentive Performance Materials Inc., Albany, NY (US)

( * ) Notice: Subject to any disclaimer, the term of this patent is extended or adjusted under 35 U.S.C. 154(b) by 209 days.

(21) Appl. No.: 12/221,175

(22) Filed: Jul. 31, 2008

(65) Prior Publication Data

US 2010/0029817 A1    Feb. 4, 2010

(51) Int. Cl.
*B60C 1/00* (2006.01)
*C07F 7/04* (2006.01)

(52) U.S. Cl. ........................... 524/262; 556/427
(58) Field of Classification Search ............... 524/262
See application file for complete search history.

(56) References Cited

U.S. PATENT DOCUMENTS 6,548,594 B2    4/2003  Luginsland et al.
6,849,754 B2    2/2005  Deschler et al.
7,560,583 B2 *  7/2009  Chaves et al. ............... 556/429

FOREIGN PATENT DOCUMENTS

WO     WO 2008/042418 A1    4/2008

OTHER PUBLICATIONS

U.S. Appl. No. 11/358,550, filed Feb. 21, 2006, Chaves, et al.
U.S. Appl. No. 11/358,818, filed Feb. 21, 2006, Chaves, et al.
U.S. Appl. No. 11/358,369, filed Feb. 21, 2006, Chaves, et al.
U.S. Appl. No. 11/358,861, filed Feb. 21, 2006, Chaves, et al.
U.S. Appl. No. 11/505,055, filed Aug. 14, 2006, Chaves, et al.
U.S. Appl. No. 11/505,166, filed Aug. 14, 2006, Chaves, et al.
U.S. Appl. No. 11/505,178, filed Aug. 14, 2006, Chaves, et al.
U.S. Appl. No. 11,104,103, filed Apr. 12, 2005, Chaves, et al.

* cited by examiner

*Primary Examiner*—Ling-Siu Choi
*Assistant Examiner*—Hui Chin
(74) *Attorney, Agent, or Firm*—Dominick G. Vicari; Joseph S. Ostroff

(57) ABSTRACT

Sulfur-containing silane and its partially to substantially complete hydrolyzate(s) are useful as additives for filled elastomeric compositions for tires and other cured rubber articles.

22 Claims, No Drawings

SULFUR-CONTAINING SILANE, FILLED ELASTOMERIC COMPOSITIONS CONTAINING SAME AND ARTICLES MADE THEREFROM

FIELD OF THE INVENTION

The present invention relates to sulfur-containing silanes, their preparation and use to make filled elastomeric compositions and articles made therefrom such as tires, belts, hoses, shoe soles, and the like. These silanes reduce or eliminate the generation of volatile organic compounds (VOCs) during use, as measured by U.S. Environmental Protection Agency Method 24, aid in the processing of filled elastomeric materials and enhance the end-use properties of articles made therefrom.

DESCRIPTION OF THE RELATED ART

Sulfur-containing silanes and their use as coupling agents in filled elastomers are known in the art. However, the heretofore known silanes are very reactive with conventional fillers and elastomers and are therefore difficult to use. When known silanes are used at levels necessary to achieve optimum coupling of filler to the host elastomer, the uncured filled elastomer typically exhibits short scorch times and poorly dispersed filler. Long scorch times are necessary for satisfactory mixing of the filler and other ingredients with the elastomer, extrusion of the uncured elastomer and fabrication of articles therefrom without premature crosslinking or formation of high viscosity compounds. Good dispersion of filler is required to achieve satisfactory end-use properties such as weatherability, wear, tear-resistance, and so on. Known silanes are also derived from monoalcohols that generate volatile organic compound (VOC) emissions during their fabrication and use. These monoalcohols pose a flammability concern when these silane coupling agents are compounded into rubber formulations at elevated temperatures. In addition, monoalcohol vapors can create undesirable microporosity in the elastomer product.

U.S. Pat. Nos. 6,548,594 and 6,849,754 describe mercaptosilane coupling agents containing $C_9$-$C_{30}$ alkoxy groups. Although these compounds offer reduced VOC emissions, the processing of rubber containing them and their performance as coupling agents do not achieve all of the desirable end-use properties for many types of articles made therefrom.

In addition to the need to reduce VOCs during the preparation of inorganic filled elastomers, a need also exists to improve the dispersion of the inorganic fillers in the elastomers while maintaining suitable processability of the compositions. Better dispersion improves the performance of cured articles made from the filled elastomers, such as tires, by reducing their rolling resistance, heat build-up and wear.

Glycol derivatives of organosilanes are known in the art. As disclosed in copending U.S. patent application Ser. Nos. 11/358,550, 11/358,818, 11/358,369, and 11/358,861, scorch, the level of VOC emissions and coupling performance of filled elastomers can be improved using organofunctional silanes or mixtures of organofunctional silanes containing both free and blocked mercaptan groups. U.S. patent application Ser. Nos. 11/505,055, 11/505,166 and 11/505,178 disclose that scorch, reduction in VOC emissions and coupling performance of filled elastomers can be improved using organofunctional silanes or mixtures of organofunctional silanes that contain both non-reactive hydrocarbyl or heterocarbyl dispersing groups and free mercaptan groups. As disclosed in U.S. patent application Ser. No. 11/104,103, reduced VOC emissions are achieved employing organofunctional silanes containing alkanedioxysilyl groups. The entire contents of aforesaid U.S. patent application Ser. Nos. 11/358,550; 11/358,818; 11/358,681; 11/505,055; 11/505,166; 11/505,178; and 11/104,103 are incorporated by reference herein.

However, there is still a need to further reduce the volatility of sulfur-containing silanes as well as the levels of monoalcohols or diols that are generated during their use while further improving the processibility and end-use properties of filled elastomers and articles made therefrom such as improved wear and greater reinforcing properties.

SUMMARY OF THE INVENTION

In one embodiment, the present invention provides sulfur-containing silane, and/or the partial to substantially complete hydrolyzate(s) of sulfur-containing silane, of general Formula (1):

$$[Y^1SG^1SiZ^\theta]_m[Y^2SG^2SiZ^\theta Z^\beta]_n[Y^3SG^3SiZ^\beta{}_3]_o$$
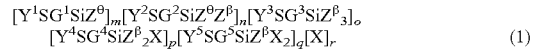
$$[Y^4SG^4SiZ^\beta{}_2X]_p[Y^5SG^5SiZ^\beta X_2]_q[X]_r \qquad (1)$$

wherein:

each occurrence of $G^1$, $G^2$, $G^3$, $G^4$ and $G^5$ is independently a hydrocarbylene group containing up to 15 carbon atoms selected from the group consisting of alkylene, alkenylene, arylene, and aralkylene groups;

each occurrence of X is independently selected from the group consisting of —R, —OR, —OC(=O)$R^3$, H-$A^2G^6$(OH)(O—), $R^1A^1C(=O)A^2G^6(OH)O$— and $[R^1A^1C(=O)A^2]_2G^6O$—, wherein each occurrence of $A^1$ is independently selected from the group consisting of a covalent chemical bond between $R^1$ and the carbonyl group, an oxygen atom and —$NR^2$—; each occurrence of $A^2$ is independently selected from a covalent chemical bond between $G^6$ and the carbonyl group, an oxygen atom and —$NR^2$—; each occurrence of R is independently selected from the group consisting of straight, cyclic and branched alkyl, alkenyl, aryl, and aralkyl groups containing up to 12 carbon atoms; each occurrence of $R^1$ is independently selected from the group consisting of hydrogen and straight, cyclic or branched alkyl, alkenyl, aryl, and aralkyl groups containing up to 18 carbon atoms; each occurrence of $R^2$ is independently selected from the group consisting of hydrogen and straight, cyclic and branched alkyl, alkenyl, aryl, and aralkyl groups containing up to 18 carbon atoms; each occurrence of $R^3$ is independently selected from the group consisting of hydrogen and straight, cyclic and branched alkyl, alkenyl, aryl, and aralkyl containing up to 30 carbon atoms;

each occurrence of $Y^1$, $Y^2$, $Y^3$, $Y^4$, and $Y^5$ is independently selected from hydrogen and an acyl group, $R^3C(=O)$—, wherein each occurrence of $R^3$ is independently selected from the group consisting of hydrogen and straight, cyclic and branched alkyl, alkenyl, aryl, and aralkyl groups containing up to 30 carbon atoms;

each occurrence of $Z^\beta$, which forms a bridging structure between two silicon atoms, is selected from the group consisting of $[R^1A^1C(=O)A^2G^6(O—)_2]_{0.5}$ and $[H-A^2G^6(O—)_2]_{0.5}$, wherein each occurrence of $A^1$ is independently selected from the group consisting of a covalent chemical bond between $R^1$ and the carbonyl group, an oxygen atom and —$NR^2$—; each occurrence of $A^2$ is independently selected from the group consisting of a covalent chemical bond between $G^6$ and the carbonyl group, an oxygen atom and —$NR^2$—; each occurrence of $R^1$ is independently selected from the group consisting of hydrogen and straight, cyclic and branched alkyl, alkenyl, aryl, and alkyl groups containing up to 18 carbon atoms; each $R^2$ is independently selected from the group consisting of hydrogen and straight, cyclic and branched alkyl, alkenyl, aryl, and aralkyl groups containing up to 18 carbon atoms; and each occurrence of $G^6$ is independently a hydrocarbylene group of from 3 to 15 carbon atoms;

each occurrence of $Z^\Theta$, which forms a cyclic structure with a silicon atom, is independently selected from the group consisting of $R^1A^1C(=O)A^2G^6(O—)_2$ and $H-A^2G^6(O—)_2$, wherein each occurrence of $A^1$ is independently selected from the group consisting of a covalent chemical bond between $R^1$ and the carbonyl group, oxygen atom and $—NR^2—$; each occurrence of $A^2$ is independently selected from the group consisting of a covalent chemical bond between $G^6$ and the carbonyl group, oxygen atom and $—NR^2—$; each occurrence of $R^1$ is independently selected from the group consisting of hydrogen and straight, cyclic and branched alkyl groups, alkenyl groups, aryl groups, and aralkyl groups containing up to 18 carbon atoms; each occurrence of $R^2$ is independently selected from the group consisting of hydrogen and straight, cyclic and branched alkyl groups, alkenyl groups, aryl groups, and aralkyl groups containing up to 18 carbon atoms; and each occurrence of $G^6$ is independently a hydrocarbylene group of from 3 to 15 carbon atoms;

each occurrence of subscripts m, n, o, p, q and r independently is an integer wherein m is 0 or 1; n is 0 to 18; o is 0 to 20; and, p is 0 to 20; q is 0 to 20 and r is 0 or 1, with the provisos that, (i) when m is 1,r is 1 and n+o+p+q is 0,
(ii) when m is 0,r is 0 and n+o+p+q is equal to or greater than 2,and
(iii) the silane contains at least one $Z^\beta$ of the structure $[R^1A^1C(=O)A^2G^6(O—)_2]_{0.5}$ or at least one $Z^\Theta$ with the structure $R^1A^1C(=O)A^2G^6(O—)_2$.

According to still other aspects of the present invention, curable filled rubber composition are provided which contain one or more silanes of Formula (1), supra, and various cured rubber articles formed therefrom, e.g., tires and components thereof such as tread and sidewall, and hoses, belts, seals, gaskets and the like.

In the specification and claims herein, the following terms and expressions are to be understood as indicated.

The expression "sulfur-containing silane" means a monomeric, dimeric, oligomeric or polymeric silane possessing at least one mercaptan or at least one thioester functionality, silane monomer containing at least one cyclic ring structure containing a silicon atom and two oxygen atoms derived from polyhydroxy-containing compounds that contain an ester, urethane, amide, urea or carbonate functionality and silane dimers, oligomers and/or polymers in which adjacent silane units are bonded to each other through bridged substituted alkanedialkoxysilane structures derived from polyhydroxy-containing compounds that contain an ester, urethane, amide, urea or carbonate functionality.

The term "elastomer" is synonymous, and therefore interchangeable, with "rubber."

The expression "coupling agent" means an agent capable of establishing an effective chemical and/or physical bond between a vulcanizable elastomer and its filler. Effective coupling agents have functional groups capable of bonding physically and/or chemically with filler, for example, between a silicon atom of the coupling agent and the hydroxyl (OH) surface groups of the filler (e.g., surface silanols in the case of silica), and, for example, sulfur atoms which are capable of bonding physically and/or chemically with the elastomer as a result of vulcanization (curing).

The expression "filler" means a substance that is added to the elastomer to either extend the elastomer or to reinforce the elastomeric network. Reinforcing fillers are materials whose moduli are higher than the organic polymer of the elastomeric composition and are capable of absorbing stress from the organic polymer when the elastomer is strained. Fillers included fibers, particulates, and sheet-like structures and can be composed of inorganic minerals, silicates, silica, clays, ceramics, carbon, organic polymers, and diatomaceous earth. The filler of the present invention can be essentially inert to the silane with which it is admixed, or it can be reactive therewith.

The expression "particulate filler" means a particle or grouping of particles that form aggregates or agglomerates. Particulate fillers that are useful herein can be essentially inert to coupling agents with which they are admixed, e.g., silane coupling agents, or they can be reactive therewith.

The term "carrier" means a porous or high surface area filler that has a high adsorption or absorption capability and is capable of carrying up to 75 percent liquid silane while maintaining its free-flowing and dry properties. Useful filler/carriers herein are essentially inert to silane coupling agents and are capable of releasing or deabsorbing liquid silanes when added to the sulfur-vulcanizable elastomeric composition.

Other than in the working examples or where otherwise indicated, all numbers expressing amounts of materials, reaction conditions, time durations, quantified properties of materials, and so forth, stated in the specification and claims are to be understood as being modified in all instances by the term "about."

It will be understood that any numerical range recited herein includes all sub-ranges within that range and any combination of the various endpoints of such ranges or subranges.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

DETAILED DESCRIPTION OF THE INVENTION

In accordance with the invention, the sulfur-containing silanes of general Formula (1) can be prepared by the process which comprises:

reacting a) at least one organofunctional silane of general Formulae (2), (3), (4), (5) and (6):

$$(Y^1S)\text{-}G^1\text{-}(SiX^1X^2X^3) \quad (2)$$

$$(Y^2S)\text{-}G^2\text{-}(SiX^1X^2X^3) \quad (3)$$

$$(Y^3S)\text{-}G^3\text{-}(SiX^1X^2X^3) \quad (4)$$

$$(Y^4S)\text{-}G^4\text{-}(SiX^1X^2X^3) \quad (5)$$

$$(Y^5S)\text{-}G^5\text{-}(SiX^1X^2X^3) \quad (6)$$

wherein:

each occurrence of $G^1$, $G^2$, $G^3$, $G^4$ and $G^5$ is independently a hydrocarbylene group containing up to 15 carbon atoms selected from the group consisting of alkylene, alkenylene, arylene and aralkylene;

each occurrence of $X^1$ is independently selected from the group consisting of 13 Cl, —Br, $R^3O—$, $R^3C(=O)O—$, $R^3{}_2C=NO—$, and $R^3{}_2NO—$, wherein each $R^3$ is independently selected from the group consisting of hydrogen and straight, cyclic and branched alkyl, alkenyl, aryl and aralkyl groups containing up to 30 carbon atoms;

each occurrence of $X^2$ and $X^3$ is independently selected from the group consisting of —Cl, —Br, $R^3O$—, $R^3C(=O)O$—, $R^3_2C=NO$—, $R^3_2NO$— and R, wherein each occurrence of R is independently selected from the group consisting of straight, cyclic and branched alkyl, alkenyl, aryl, and aralkyl groups containing up to 12 carbon atoms, and each occurrence of $R^3$ is independently selected from the group consisting of hydrogen, and straight, cyclic and branched alkyl, alkenyl, aryl, and aralkyl groups containing up to 30 carbon atoms;

each occurrence of $Y^1$, $Y^2$, $Y^3$, $Y^4$, and $Y^5$ is independently selected from the group consisting of hydrogen and an acyl group, $R^3C(=O)$—, wherein each occurrence of $R^3$ is independently selected from the group consisting of hydrogen and straight, cyclic and branched alkyl, alkenyl, aryl, and aralkyl groups containing up to 30 carbon atoms; with b) one or more dihydroxyl-containing compounds of general Formula (7):

$$R^1A^1C(=O)A^2G^6(OH)_2, \quad (7)$$

wherein $A^1$ is selected from the group consisting of a covalent chemical bond between $R^1$ and the carbonyl group, an oxygen atom and —$NR^2$—; $A^2$ is selected from the group consisting of a covalent chemical bond between $G^6$ and the carbonyl group, an oxygen atom and —$NR^2$—; $R^1$ is selected from the group consisting of hydrogen and straight, cyclic and branched alkyl, alkenyl, aryl, and aralkyl groups containing up to 18 carbon atoms; $R^2$ is selected from the group consisting of hydrogen and straight, cyclic and branched alkyl, alkenyl, aryl, and aralkyl groups containing up to 18 carbon atoms; and, $G^6$ is a hydrocarbylene group of from 3 to 15 carbon atoms;

c) optionally, with one or more monohydroxy-containing compounds of general Formula (8):

$$[R^1A^1C(=O)A^2]_2G^6OH, \quad (8)$$

wherein each occurrence $A^1$ is independently selected from the group consisting of a covalent chemical bond between $R^1$ and the carbonyl group, an oxygen atom and —$NR^2$—; each occurrence of $A^2$ is independently selected from the group consisting of a covalent chemical bond between $G^6$ and the carbonyl group, an oxygen atom and —$NR^2$—; each occurrence of $R^1$ is independently selected from the group consisting of hydrogen and straight, cyclic and branched alkyl, alkenyl, aryl, and aralkyl groups containing up to 18 carbon atoms; each occurrence of $R^2$ is independently selected from the group consisting of hydrogen and straight, cyclic and branched alkyl groups, alkenyl groups, aryl groups, and aralkyl groups containing up to 18 carbon atoms; and, $G^6$ is a hydrocarbylene group of from 3 to 15 carbon atoms; and, d) optionally, with one or more dihydroxyl- and/or trihydroxyl-containing compounds of general Formula (9):

$$H-A^2G^6(OH)_2 \quad (9)$$

wherein $A^2$ is selected from the group consisting of an oxygen atom and —$NR^2$— wherein $R^2$ is selected from the group consisting of hydrogen and straight, cyclic and branched alkyl, alkenyl, aryl and aralkyl groups containing up to 18 carbon atoms; and, $G^6$ is a hydrocarbylene group of from 3 to 15 carbon atoms; to provide sulfur-containing silane of Formula (1).

In one embodiment herein, in a sulfur-containing silane dimer, oligomer, or polymer, each silane unit therein is bonded to an adjacent silane unit through a bridging group resulting from the reaction of the selected silane monomer(s) with one or more dihydroxyl-containing compounds of general Formula (7):

$$R^1A^1C(=O)A^2G^6(OH)_2, \quad (7)$$

wherein $A^1$ is a covalent chemical bond between $R^1$ and the carbonyl group, an oxygen atom or —$NR^2$, and preferably a covalent chemical bond between $R^1$ and the carbonyl group; $A^2$ is a covalent chemical bond between $G^6$ and the carbonyl group, an oxygen atom or —$NR^2$—, and preferably an oxygen atom; $R^1$ is selected from the group consisting of hydrogen and straight, cyclic and branched alkyl, alkenyl, aryl, and aralkyl groups containing up to 18 carbon atoms, preferably a straight or branched alkyl group of from 3 to 12 carbon atom and more preferably a straight chain alkyl group of from 6 to 10 carbon atoms; $R^2$ is selected from the group consisting of hydrogen and straight, cyclic and branched alkyl, alkenyl, aryl, and aralkyl groups containing up to 18 carbon atoms; and $G^6$ is a hydrocarbylene group of from 3 to 15 carbon atoms, and preferably a trivalent alkylene group of from 3 to 8 carbon atoms.

In one embodiment herein, the dihydroxyl-containing compound of Formula (7) has its two hydroxyl groups covalently bonded to two different carbon atoms that are covalently bonded to each other by a single bond and the $R^1A^1C(=O)A^2$- group is bonded to a carbon atom of $G^6$ that does not contain a hydroxyl group.

Some representative non-limiting examples of dihydroxyl compounds of Formula (7) are acetic acid 2,3-dihydroxy-propyl ester, octanoic acid 2,3-dihydroxy-propyl ester, octanoic acid (2,3-dihydroxy-propyl)-amide, 1-(2,3-dihydroxy-propyl)-3-hexyl-urea, carbonic acid 2,3-dihydroxy-propyl ester hexyl ester, 2-ethyl-hexanoic acid 2,3-dihydroxy-propyl ester, benzoic acid 2,3-dihydroxy-propyl ester, phenyl-carbamic acid 2,3-dihydroxy-propyl ester, propionic acid 3-hydroxy-2-hydroxymethyl-propyl ester, propionic acid 3-hydroxy-2-hydroxymethyl-2-methyl-propyl ester, propionic acid 2,2-bis-hydroxymethyl-butyl ester, hexanoic acid 2,2-bis-hydroxymethyl-butyl ester, octanoic acid 2,2-bis-hydroxymethyl-butyl ester, 2-ethyl-hexanoic acid 2,2-bis-hydroxymethyl-butyl ester, phenyl-acetic acid 2,2-bis-hydroxymethyl-butyl ester, 2-methyl-acrylic acid 2,2-bis-hydroxymethyl-butyl ester, benzoic acid 2,2-bis-hydroxymethyl-butyl ester, cyclohexane carboxylic acid 2,2-bis-hydroxymethyl-butyl ester, hexanoic acid 3,4-dihydroxy-butyl ester, and mixtures thereof.

In one embodiment of the general preparative process described above for making sulfur-containing silane of Formula (1), at least one organofunctional silane selected from among Formulae (2), (3), (4), (5) and/or (6) is transesterified with at least one dihydroxyl-containing compound of Formula (7), optionally, with a monoalcohol of Formula (8), and, optionally, with at least one dihydroxyl-compound and/or trihydroxyl-containing compound of Formula (9), optionally, in the presence of one or more known or conventional transesterification catalysts such as para-toluenesulfonic acid, to provide sulfur-containing silane of Formula (1).

In one application of the foregoing process embodiment, at least one organofunctional silane of Formulae (2), (3), (4), (5), and/or (6) wherein:

each occurrence of $G^1$, $G^2$, $G^3$, $G^4$ and $G^5$ is independently a hydrocarbylene group containing up to 15 carbon atoms, more specifically a straight or branched chain alkylene group of from 1 to 6 carbon atoms, even more specifically from 1 to 3 carbon atoms, and still more specifically 3 carbon atoms;

each R is independently selected from the group consisting of straight, cyclic and branched alkyl, alkenyl, aryl and aralkyl containing up to 12 carbon atoms, more specifically a straight chain alkyl group containing 1 to 6 carbon atoms, and more specifically methyl;

each occurrence of $Y^1, Y^2, Y^3, Y^4$, and $Y^5$ is independently selected form hydrogen and an acyl group of from 1 to 30 carbon atoms, more specifically, from 6 to 12 carbon atoms, and still more specifically from 6 to 8 carbon atoms; is transesterified with at least one dihydroxyl-containing compound of Formula (7), wherein:

$A^1$ is selected from the group consisting of a covalent chemical bond between $R^1$ and the carbonyl group, an oxygen atom and $-NR^2-$, and more specifically a covalent chemical bond between $R^1$ and the carbonyl group; $A^2$ is a covalent chemical bond between $R^1$ and the carbonyl group, an oxygen atom and $-NR^2-$, and more specifically an oxygen atom; $R^1$ is selected from the group consisting of hydrogen and a straight, cyclic and branched alkyl, alkenyl, aryl, and aralkyl groups containing up to 18 carbon atoms, more specifically an alkyl group containing from 2 to 12 carbon atoms, and even more specifically, an alkyl group containing from 4 to 8 carbon atoms; $R^2$ is selected from the group consisting of hydrogen and straight, cyclic and branched alkyl, alkenyl, aryl, and aralkyl groups containing up to 18 carbon atoms, more specifically, alkyl of from 1 to 6 carbon atoms, and even more specifically methyl; $G^6$ is independently a hydrocarbylene group of from 3 to 15 carbon atoms, and more specifically a trivalent alkylene group of from 3 to 6 carbon atom considered derived from an alkane in which only one hydrogen on the carbon is substituted with a hydroxyl group or $R^1A^1C(=O)A^2$- group; and optionally in the presence of transesterification catalyst(s) such as aforementioned para-toluenesulfonic acid, to provide sulfur-containing silane of Formula (1):

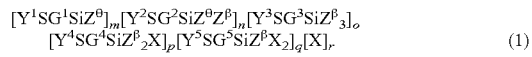
(1)

wherein:

each occurrence of $G^1, G^2, G^3, G^4$ and $G^5$ is independently a hydrocarbylene group containing up to 15 carbon atoms selected from the group consisting of alkylene, alkenylene, arylene, and aralkylene groups, more specifically a straight or branched chain alkylene group of from 1 to 6 carbon atoms, even more specifically an alkylene group of from 1 to 3 carbon atoms, and still more specifically an alkylene group of 3 carbon atoms;

each occurrence of X is independently selected from the group consisting of $-R$, $[R^1A^1C(=O)A^2]_2G^6O-$ and $R^1A^1C(=O)A^2G^6(OH)O-$, wherein each $A^1$ is independently selected from the group consisting of a covalent chemical bond between $R^1$ and the carbonyl group, an oxygen atom and $-NR^2-$, and more specifically a covalent bond between $R^1$ and the carbonyl group; each $A^2$ is independently selected from a covalent chemical bond between $G^6$ and the carbonyl group, an oxygen atom and $-NR^2-$, and more specifically an oxygen atom; each $R^1$ is independently selected from the group consisting of hydrogen and straight, cyclic and branched alkyl, alkenyl, aryl, and aralkyl groups containing up to 18 carbon atoms, more specifically an alkyl group containing from 2 to 12 carbon atoms, and even more specifically, an alkyl group containing from 4 to 8 carbon atoms; each $R^2$ is independently selected from the group consisting of hydrogen and straight, cyclic and branched alkyl, alkenyl, aryl, and aralkyl groups containing up to 18 carbon atoms, more specifically, a hydrogen and an alkyl group containing from 1 to 6 carbon atoms, and even more specifically methyl; and each $G^6$ is independently a hydrocarbylene group of from 3 to 15 carbon atoms, and more specifically a trivalent alkylene group of from 3 to 6 carbon atoms considered as derived from an alkane;

each occurrence of $Y^1, Y^2, Y^3, Y^4$, and $Y^5$ is independently selected from hydrogen and an acyl group, $R^3C(=O)-$, wherein $R^3$ is selected from the group consisting of a hydrogen and a straight, cyclic and branched alkyl, alkenyl aryl and aralkyl groups of from up to 30 carbon atoms, more specifically an alkyl group of from 6 to 12 carbon atoms, and more specifically, an alkyl group of from 6 to 8 carbon atoms;

each occurrence of $Z^\beta$, which forms a bridging structure between two silicon atoms, is $[R^1A^1C(=O)A^2G^6(O-)_2]_{0.5}$, wherein each $A^1$ is independently selected from the group consisting of a covalent chemical bond between $R^1$ and the carbonyl group, oxygen atom and $-NR^2-$, and more specifically a covalent bond between $R^1$ and the carbonyl group; each $A^2$ is independently selected from the group consisting of a covalent chemical bond between $G^6$ and the carbonyl group, oxygen atom and $-NR^2-$, and more specifically an oxygen atom; each $R^1$ is independently selected from the group consisting of hydrogen and straight, cyclic and branched alkyl, alkenyl, aryl, and aralkyl groups containing up to 18 carbon atoms, more specifically an alkyl group containing from 2 to 12 carbon atoms, and even more specifically, an alkyl group containing from 4 to 8 carbon atoms; each $R^2$ is independently selected from the group consisting of hydrogen and straight, cyclic and branched alkyl, alkenyl, aryl, and aralkyl groups containing up to 18 carbon atoms, more specifically, hydrogen and an alkyl group containing from 1 to 6 carbon atoms, and even more specifically methyl; and $G^6$ is independently a hydrocarbylene group of from 3 to 15 carbon atoms, and more specifically, a trivalent alkylene group of from 3 to 6 carbon atoms considered as derived from an alkane;

each occurrence of $Z^\Theta$, which forms a cyclic structure with a silicon atom, is $R^1A^1C(=O)A^2G^6(O-)_2$, wherein each $A^1$ is independently selected from the group consisting of a covalent chemical bond between $R^1$ and the carbonyl group, an oxygen atom and $-NR^2-$, and more specifically a covalent bond between $R^1$ and the carbonyl group; $A^2$ is selected form the group consisting of a covalent chemical bond between $G^6$ and the carbonyl group, an oxygen atom and $-NR^2-$, and more specifically an oxygen atom; each $R^1$ is independently selected from the group consisting of hydrogen and straight, cyclic and branched alkyl, alkenyl, aryl, and aralkyl groups containing up to 18 carbon atoms, more specifically an alkyl group containing from 2 to 12 carbon atoms, and even more specifically, an alkyl group containing from 4 to 8 carbon atoms; $R^2$ is selected from the group consisting of hydrogen and straight, cyclic and branched alkyl, alkenyl, aryl, and aralkyl groups containing up to 18 carbon atoms, more specifically, an alkyl group containing from 1 to 6 carbon atoms, and even more specifically methyl; and each $G^6$ is independently a hydrocarbylene group of from 3 to 15 carbon atoms, and more specifically, a trivalent alkylene group of from 3 to 6 carbon atoms considered as derived from an alkane;

each occurrence of subscripts m, n, o, p, q and r independently is an integer wherein m is 0 or 1; n is 0 to 18; o is 0 to 20; p is 0 to 20; q is 0 to 20; and r is 0 or 1, with the provisos that (i) when m is 1, r is 1 and n+o+p+q is 0.

(ii) when m is 0, r is 0 and n+o+p+q is equal to or greater than 2, more specifically, m is 0; n is 0 to 6, o is 0 to 6, p is 0 to 6, q is 0 to 6 and r is 0 with the provisos that n+o+p+q is an integer between 2 and 10, and more specifically, m is 1; r is 1 and n, o, p, and q are 0, and, (iii) the silane contains at least one $Z^\beta$ of the structure $[R^1A^1C(=O)A^2G^6(O—)_2]_{0.5}$ or at least one $Z^\Theta$ of the structure $R^1A^1C(=O)A^2G^6(O—)_2$.

In another specific embodiment, each occurrence of $G^1$, $G^2$, $G^3$, $G^4$ and $G^5$ independently is a divalent straight or branched chain alkylene group of from 1 to 6 carbon atoms, more specifically from 1 to 4 carbon atoms and still more specifically 2 or 3 carbon atoms.

In another embodiment, at least one $G^1$, $G^2$, $G^3$, $G^4$ and $G^4$ group is different from another $G^1$, $G^2$, $G^3$, $G^4$, and $G^5$ group and each occurrence of $G^1$, $G^2$, $G^3$, $G^4$ and $G^5$ independently is a hydrocarbylene group containing from 1 to 15 carbon atoms, more specifically a straight or branched chain alkylene group of from 1 to 6 carbon atoms, still more specifically a straight or branched chain alkylene group of from 1 to 4 carbon atoms and yet still more specifically a straight chain alkylene group of 2 or 3 carbon atoms.

In another embodiment, m and r are 0, at least one $Y^1$, $Y^2$, $Y^3$, $Y^4$, and $Y^5$ group is hydrogen and at least one other of these groups is an acyl group containing up to 30 carbon atoms, more specifically, from 3 to 12 carbon atoms, and even more specifically, from 6 to 8 carbon atoms.

In still another embodiment, at least one $Y^1$, $Y^2$, $Y^3$, $Y^4$, and $Y^5$ group is hydrogen and at least one $Y^1$, $Y^2$, $Y^3$, $Y^4$, and $Y^5$ group is an acyl group containing up to 30 carbon atoms. The molar ratio of hydrogen to acyl group for the $Y^1$, $Y^2$, $Y^3$, $Y^4$, and $Y^5$ groups is from 1/50 to 50/1, more specifically from 1/10 to 10/1, and most specifically, from 1/2 to 2/1.

Some suitable reaction conditions for preparing sulfur-containing silanes of Formula (1) and their mixtures are fairly broad and include molar ratios of silane(s), determined by adding the individual molar contribution of silanes of Formulae (2), (3), (4), (5) and/or (6), and polyhydroxy-containing compound(s) of Formula (7), of from 0.3 to 3 moles of compound of Formula (7) per mole of silyl group, more specifically from 0.5 to 2 moles of compound of Formula (7) per mole of silyl group, and still more specifically from 1 to 1.5 moles of Formula (7) per mole of silyl group, at a temperature of from 0° C. to 150° C., a pressure of from 0.1 to 2,000 mmHg, and in the optional presence of catalyst(s) and/or solvent(s).

As used herein in connection with silanes of Formula (1), "substituted alkanedialkoxy" refers to hydrocarbon-based diols containing an ester, urethane, amide, urea or carbonate functionality in which the hydrogen atoms of the two hydroxyl groups have been removed to provide divalent radicals, and whose structures are represented by general Formula (10):

$$R^1A^1C(=O)A^2G^6(O—)_2, \quad (10)$$

wherein $R^1$, $A^1$, $A^2$ and $G^6$ are as defined herein.

As used herein in connection with silanes of Formula (1), "cyclic dialkoxy" refers to a silane or group in which cyclization is about a silicon atom by two oxygen atoms each of which is attached to a common divalent hydrocarbon group such as is commonly the case with diols. Cyclic dialkoxy groups herein are represented by $Z^\Theta$ which is important in the formation of the cyclic structure. Branched and more sterically hindered $G^6$ groups tend to promote the formation of cyclic structures containing a silicon atom.

In yet a further embodiment herein in connection with silanes of Formula (1), "bridging dialkoxy" refers to a silane or group in which two different silicon atoms are each bound to one oxygen atom, which in turn is bound to a common divalent hydrocarbon group such as is commonly found in diols. Bridging dialkoxy groups herein are represented by $Z^\beta$.

In still a further embodiment herein in connection with silanes of Formula (1), "hydroxyalkoxy" refers to a silane or group in which one OH hydrogen atom has been removed to provide a monovalent radical, and whose structure is represented by general Formulae (11) and (12):

$$R^1A^1C(=O)A^2G^6(OH)O— \quad (11)$$

$$H-A^1G^6(OH)O— \quad (12)$$

and "substituted-alkoxy" refers to a silane or group in which one OH hydrogen atom has been removed to provide a monovalent radical, and whose structure is represented by the general Formulae (13) and (14):

$$[R^1A^1C(=O)A^2]_2G^6O— \quad (13)$$

$$[H-A^2]_2G^6O— \quad (14).$$

Hydroxyalkoxy and substituted-alkoxy groups herein are represented by X.

In connection with $Z^\beta$, the notations $[R^1A^1C(=O)A^2G^6(O—)_2]_{0.5}$ and $[H-A^2G^6(O—)_2]_{0.5}$, refer to one-half of a bridging substituted alkanedialkoxy group which can bond to different silyl groups present in the sulfur-containing silanes of Formula (1). These notations are used in conjunction with a silicon atom and they are taken herein to mean that one-half of a substituted alkanedialkoxy group is bonded to the associated silicon atom. It is understood that the other half of the substituted alkanedialkoxy group is bonded to a silicon atom that occurs somewhere else in the overall molecular structure being described. Thus, the $[R^1A^1C(=O)A^2G^6(O—)_2]_{0.5}$ or $[H-A^2G^6(O—)_2]_{0.5}$ group mediate the chemical bonds that hold two separate silicon atoms together. In the case where $[R^1A^1C(=O)A^2G^6(O—)_2]_{0.5}$ or $[H-A^2G^6(O—)_2]_{0.5}$ is unsymmetrical, either end of $[R^1A^1C(=O)A^2G^6(O—)_2]_{0.5}$ or $[H-A^2G^6(O—)_2]_{0.5}$ can be bonded to either of the two silicon atoms required to complete the structures of silanes of Formula (1).

As used herein in connection with silanes of Formulae (2), (3), (4), (5), and (6), "alkyl" includes straight, branched and cyclic alkyl groups; "alkenyl" includes any straight, branched, or cyclic alkenyl group containing one or more carbon-carbon double bond, where the point of substitution can be either at a carbon-carbon double bond or elsewhere in the group; "aryl" includes the non-limiting group of any aromatic hydrocarbon from which one hydrogen atom has been removed; "aralkyl" includes, but is not limited to, any of the aforementioned alkyl groups in which one or more hydrogen atoms have been substituted by the same number of like and/or different aryl (as defined herein) substituents. Specific examples of alkyls include, but are not limited to, methyl, ethyl, propyl and isobutyl. Specific examples of alkenyls include, but are not limited to, vinyl, propenyl, allyl, methallyl, ethylidenyl norbornane, ethylidene norbornyl, ethylidenyl norbornene and ethylidene norbornenyl. Specific examples of aryls include, but are not limited to, tolyl, xylyl, phenyl and naphthalenyl. Specific examples of aralkyls include, but are not limited to, benzyl and phenethyl.

As used herein, in connection with silanes of Formulae (2), (3), (4), (5), and (6), "cyclic alkyl" and "cyclic alkenyl" also include bicyclic, tricyclic, and higher cyclic structures, as well as the aforementioned cyclic structures further substituted with alkyl and/or alkenyl groups. Representative examples of "cyclic alkyl", "cyclic alkenyl" groups include, but are not limited to, norbornyl, norbornenyl, ethylnorbornyl, ethylnorbornenyl, ethylcyclohexyl, ethylcyclohexenyl, cyclohexylcyclohexyl and cyclododecatrienyl.

In another embodiment herein, the silane is one described by Formula (1) in which each of $G^1$, $G^2$, $G^3$, $G^4$ and $G^5$ is independently a divalent group derived by substitution of $C_1$-$C_{12}$ alkyl; X is —R and/or —OR in which R is methyl, ethyl, $[R^1A^1C(=O)A^2]_2G^6O$—, and/or $R^1A^1C(=O)A^2G^6(OH)O$—; $Z^\beta$ is $[R^1A^1C(=O)A^2G^6(O-)_2]_{0.5}$ and $Z^\Theta$ is $R^1A^1C(=O)A^2G^6(O-)_2$ in which $R^1$, $A^1$, $A^2$, and $G^6$ are as previously defined, m and r are 1, and more preferably, m and r are 0 and n+o+p+q is equal to or greater than 2.

It may be advantageous to react (a) at least one silane of Formula (2), (3), (4), (5) and/or (6) with a mixture of (b) at least one dihydroxy-containing compound of general Formula (7) and (c) at least one monohydroxyl-containing compound of general Formula (8) which operates as a chain stopper to control the degree of polymerization of the product silane(s). In this embodiment, the ratio of compounds (b) and (c) can range from 20:1 to 1:20, preferably from 5:1 to 1:5 and more preferably from 2:1 to 1:2.

In another embodiment, the reaction mixture of (b) and (c) further comprises at least one dihydroxyl- and/or trihydroxyl-containing compound of Formula (9):

$$H\text{-}A^2G^6(OH)_2 \qquad (9)$$

wherein $A^2$ is selected from the group consisting of an oxygen atom or —$NR^2$—; each $G^6$ is independently a hydrocarbylene group of from 3 to 15 carbon atoms and each $R^2$ is independently selected form the group consisting of hydrogen and straight, cyclic and branched alkyl, alkenyl, aryl and aralkyl groups containing up to 18 carbon atoms. The compound of Formula (9) can react with the at least one silane of Formulae (1) to (6) to form an endstopper, as represented by X, a bridging group, as represented by $Z^\beta$, or a group that forms a cyclic structure with a silicon atom, as represented by $Z^\Theta$. When the reaction mixture of (b) and (c) further comprises component (d), the ratios of (b): (c): (d) can suitably range from 1:20:20 to 20:20:1, preferably from 1:10:10 to 10:10:1 and more preferably from 1:5:5 to 5:5:1.

Some representative examples of $G^1$, $G^2$, $G^3$, $G^4$ and $G^5$ include those selected from the group consisting of branched alkylene groups of 1 to 15 carbon atoms such as —$CH_2(CH_2)_4CH(CH_2CH_3)CH_2$—, —$CH_2CH_2CH(CH_2CH_3)CH_2$—, —$CH_2CH(CH_3)CH_2$—, —$CH_2CH_2CH(CH_3)CH_2$—, and —$CH_2(CH_2)_4CH(CH_3)CH_2$—; diethylene cyclohexane; phenylene; any of the structures derivable from divinylbenzene such as the —$CH_2CH_2(C_6H_4)CH_2CH_2$— and —$CH_2CH_2(C_6H_4)CH(CH_3)$—, where the notation $C_6H_4$ denotes a disubstituted benzene ring; any of the structures derivable from dipropenylbenzene such as $CH_2CH(CH_3)(C_6H_4)CH(CH_3)CH_2$— where the notation $C_6H_4$ denotes a disubstituted benzene ring; any of the structures derivable from piperylene such as —$CH_2CH_2CH_2CH(CH_3)$—, —$CH_2CH_2CH(CH_2CH_3)$—, and —$CH_2CH(CH_2CH_2CH_3)$—; any of the isomers of —$CH_2CH_2$-norbornyl-; any of the monounsaturated structures derivable from myrcene containing a trisubstituted C=C, such as the non-limiting examples of —$CH_2CH[CH_2CH_2CH=C(CH_3)_2]CH_2CH_2$—, —$CH_2CH[CH_2CH_2CH=C(CH_3)_2]CH(CH_3)$—, —$CH_2C[CH_2CH_2CH=C(CH_3)_2](CH_2CH_3)$—, —$CH_2CH_2CH[CH_2CH_2CH=C(CH_3)_2]CH_2$—, —$CH_2CH_2C(—)(CH_3)[CH_2CH_2CH=C(CH_3)_2]$, and —$CH_2CH[CH(CH_3)[CH_2CH_2CH=C(CH_3)_2]]$—; and any of the monounsaturated structures derivable from myrcene lacking a trisubstituted C=C such as the non-limiting examples of —$CH_2CH(CH=CH_2)CH_2CH_2CH_2C(CH_3)_2$—, —$CH_2CH(CH=CH_2)CH_2CH_2CH[CH(CH_3)_2]$—, —$CH_2C(=CH—CH_3)CH_2CH_2CH_2C(CH_3)_2$—, —$CH_2C(=CH—CH_3)CH_2CH_2CH[CH(CH_3)_2]$—, —$CH_2CH_2C(=CH_2)CH_2CH_2CH_2C(CH_3)_2$—, —$CH_2CH_2C(=CH_2)CH_2CH_2CH[CH(CH_3)_2]$—, —$CH_2CH=C(CH_3)_2CH_2CH_2CH_2C(CH_3)_2$— and —$CH_2CH=C(CH_3)_2CH_2CH_2CH[CH(CH_3)_2]$; —$(CH_2)_g$— wherein g is an integer of from 1 to 15, which represent terminal straight-chain alkyls further substituted terminally at the other end such as —$CH_2$—, —$CH_2CH_2$—, —$CH_2CH_2CH_2$—, and —$CH_2CH_2CH_2CH_2CH_2CH_2CH_2CH_2$—; their beta-substituted analogs such as —$CH_2(CH_2)_iCH(CH_3)$— where i is preferably 0 to 12; methyl substituted alkylene groups such as the non-limiting examples of —$CH_2CH_2$-methylcyclohexyl-, —$CH_2CH_2C(CH_3)_2CH_2$— and —$CH_2CH(CH_3)CH_2$—; any of the structures derivable from isoprene such as —$CH_2CH(CH_3)CH_2CH_2$—, —$CH_2CH(CH_3)CH(CH_3)$—, —$CH_2C(CH_3)(CH_2CH_3)$—, —$CH_2CH_2CH(CH_3)CH_2$—, —$CH_2CH_2C(CH_3)_2$— and —$CH_2CH[CH(CH_3)_2]$—; any of the structures derivable from butadiene such as —$CH_2CH_2CH_2CH_2$—, —$CH_2CH_2CH(CH_3)$—, and —$CH_2CH(CH_2CH_3)$—; and, any of the diradicals obtainable from norbornane, cyclohexane or cyclopentane by the loss of two hydrogen atoms.

In yet another embodiment herein, $G^1$, $G^2$, $G^3$, $G^4$ and $G^5$ is —$CH_2CH_2CH_2$—, X is —$OCH_2C(CH_2CH_3)(OC(=O)C_7H_{15})CH_2OH$ and/or ethoxy, $Z^\beta$ is [—$OCH_2C(CH_2CH_3)(OC(=O)C_7H_{15})CH_2O$—]$_{0.5}$ and $Z^\beta$ is —$OCH_2C(CH_2CH_3)(OC(=O)C_7H_{15})CH_2O$—.

It may be advantageous to maintain the cyclic-substituted alkanedialkoxy content of the silanes herein sufficiently high relative to the total substituted alkanedialkoxy content present in order to prevent excessive crosslinking which would lead to gellation. Preferably, the cyclic-substituted alkanedialkoxy silyl content of the silanes can range from 10 to 100, specifically from 25 to 90 and, more specifically, from 50 to 70, mole percent of the total concentration of silyl groups. Excessive crosslinking can also be avoided if X in the structure of Formula (1) is sufficiently large, such as the case where p and q are from 1 to 5 and/or when the number of fragments $[Y^3SG^3Z^\beta_3]$ in the structure of Formula (1) is low, specifically, when o is 0 or 1.

Some representative examples of the sulfur-containing silanes of formula (1) include: hexanoic acid 2-(3-butyrylsulfanyl-propyl)-5-ethyl-2-methyl-[1,3,2]dioxasilinan-5-yl ester, hexanoic acid 2-(3-butyrylsulfanyl-propyl)-5-ethyl-2-ethoxy-[1,3,2]dioxasilinan-5-yl ester, hexanoic acid 2-(3-butyrylsulfanyl-propyl)-2-(3-hexanoyloxy-4-hydroxy-propoxy)-[1,3,2]dioxasilinan-5-yl ester, octanoic acid 2-(3-hexanoyloxymethyl-4-hydroxy-3-methyl-propoxy)-2-(3-hexanoylsulfanyl-propyl)-5-methyl-[1,3,2]dioxasilinan-5-ylmethyl ester, octanoic acid 2-(3-hexanoyloxymethyl-4-hydroxy-3-methyl-propoxy)-2-(3-mercapto-propyl)-5-methyl-[1,3,2]dioxasilinan-5-ylmethyl ester, 2-ethylhexanoic acid 2-[3-(2-ethyl-hexanoyloxymethyl)-4-hydroxy-3-methyl-propoxy]-2-[3-(2-ethyl-hexanoylsulfanyl)-propyl]-5-methyl-[1,3,2]dioxasilinan-5-ylmethyl ester, 2-ethyl-hexanoic acid 2-[4-(2-ethyl-hexanoyloxy)-3-methyl-butoxy]-2-[3-(2-ethyl-hexanoylsulfanyl)-propyl]-5-methyl-[1,3,2]dioxasilinan-5-ylmethyl ester, octanoic acid 5-ethyl-2-(3-mercapto-propyl)-2-methyl-[1,3,2]dioxasilinan-5-yl ester, octanoic acid 2-ethoxy-5-ethyl-2-(3-mercapto-propyl)-[1,3,2]dioxasilinan-5-yl ester, octanoic acid 2-(2,2-bis-hydroxymethyl-butoxy)-5-ethyl-2-(3-mercapto-propyl)-[1,3,2]dioxasilinan-5-yl ester, octanoic acid 5-ethyl-2-(2-hydroxymethyl-2- octanoyloxymethyl-butoxy)-2-(3-mercapto-propyl)-[1,3,2]dioxasilinan-5-yl ester, octanoic acid 2-(2,2-bis-octanoyloxymethyl-butoxy)-5-ethyl-2-(3-mercapto-propyl)-[1,3,2]dioxasilinan-5-yl ester, octanoic acid 2-(2,2-bis-octanoyloxymethyl-butoxy)-5-ethyl-2-(3-octanoylsulfanyl-propyl)-[1,3,2]dioxasilinan-5-yl ester, octanoic acid 5-ethyl-2-(2-hydroxymethyl-2-octanoyloxymethyl-butoxy)-2-(3-octanoylsulfanyl-propyl)-[1,3,2]dioxasilinan-5-yl ester, octanoic acid 5-ethyl-2-{2-[5-ethyl-5-hydroxymethyl-2-(3-mercapto-propyl)-[1,3,2]dioxasilinan-2-yloxymethyl]-2-octanoyloxymethyl-butoxy}-2-(3-octanoylsulfanyl-propyl)-[1,3,2]dioxasilinan-5-yl ester, octanoic acid 5-ethyl-2-{2-[5-ethyl-5-octanoyloxymethyl-2-(3-octanoylsulfanyl-propyl)-[1,3,2]dioxasilinan-2-yloxymethyl]-2-octanoyloxymethyl-butoxy}-2-(3-octanoylsulfanyl-propyl)-[1,3,2]dioxasilinan-5-yl ester, octanethioic acid 3-(5-ethyl-2-{2-ethyl-4-(3-ethyl-3-methyl-heptanoylamino)-2-(octanoylamino-methyl)-3-[2-(3-octanoylsulfanyl-propyl)-[1,3,2]dioxasilinan-2-yloxy]-butoxy}-5-octanoylamino-[1,3,2]dioxasilinan-2-yl)-propyl ester, octanethioic acid 3-(5-ethyl-2-{2-ethyl-4-hexyloxycarbonyloxy-2-hexyloxycarbonyloxymethyl-3-[2-(3-octanoyl-sulfanyl-propyl)-[1,3,2]dioxasilinan-2-yloxy]-butoxy}-5-hexyloxycarbonyloxymethyl-[1,3,2]dioxasilinan-2-yl)-propyl ester, octanethioic acid 3-(5-ethyl-2-{2-ethyl-4-hexylcarbamoyloxy-2-hexylcarbamoyloxymethyl-3-[2-(3-octanoylsulfanyl-propyl)-[1,3,2]dioxasilinan-2-yloxy]-butoxy}-5-hexylcarbamoyloxymethyl-[1,3,2]dioxasilinan-2-yl)-propyl ester, octanethioic acid 3-(5-ethyl-2-{2-ethyl-4-hexylcarbamoyloxy-2-hexylcarbamoyloxymethyl-3-[2-(3-mercapto-propyl)-[1,3,2]dioxasilinan-2-yloxy]-butoxy}-5-hexylcarbamoyloxymethyl-[1,3,2]dioxasilinan-2-yl)-propyl ester, acetic acid 2-[ethoxy-(4-mercapto-butyl)-methyl-silanyloxymethyl]-2-[ethoxy-(3-mercapto-propyl)-methyl-silanyloxymethyl]-butyl ester, N-{2-[ethoxy-(4-mercapto-butyl)-methyl-silanyloxymethyl]-2-[ethoxy-(3-mercapto-propyl)-methyl-silanyloxymethyl]-butyl}-acetamide, carbonic acid 2-[ethoxy-(4-mercapto-butyl)-methyl-silanyloxymethyl]-2-[ethoxy-(3-mercapto-propyl)-methyl-silanyloxymethyl]-butyl ester propyl ester, thioacetic acid S-[3-(ethoxy-{2-[ethoxy-(4-mercapto-butyl)-methyl-silanyloxymethyl]-2-propoxycarbonyloxymethyl-butoxy}-methyl-silanyl)-propyl]ester, thioacetic acid S-[3-(ethoxy-{2-[ethoxy-(4-mercapto-butyl)-ethoxy-silanyloxymethyl]-2-propoxycarbonyloxymethyl-butoxy}-ethoxy-silanyl)-propyl]ester, acetic acid 2-{2-acetoxymethyl-2-[{2-acetoxymethyl-2-[ethoxy-(3-mercapto-propyl)-methyl-silanyloxymethyl]-butoxy}-(3-acetylsulfanyl-propyl)-methyl-silanyloxymethyl]-butoxy}-5-ethyl-2-(3-mercapto-propyl)-[1,3,2]dioxasilinan-5-ylmethyl ester, octanoic acid 2-{2-octanoyloxymethyl-2-[{2-octanoyloxymethyl-2-[ethoxy-(3-mercapto-propyl)-methyl-silanyloxymethyl]-butoxy}-(3-octanonylsulfanyl-propyl)-methyl-silanyloxymethyl]-butoxy}-5-ethyl-2-(3-mercapto-propyl)-[1,3,2]dioxasilinan-5-ylmethyl ester, acetic acid 2-[{2-acetoxymethyl-2-[ethoxy-(3-mercapto-propyl)-ethoxy-silanyloxymethyl]-butoxy}-(3-acetylsulfanyl-propyl)-ethoxy-silanyloxymethyl]-2-[ethoxy-(3 -mercapto-propyl)-methyl-silanyloxymethyl]-butyl ester, acetic acid 2-[{2-acetoxymethyl-2-[ethoxy-(3-mercapto-propyl)-methyl-silanyloxymethyl]-butoxy}-(3-acetylsulfanyl-propyl)-methyl-silanyloxymethyl]-2-[(3-acetylsulfanyl-propyl)-ethoxy-methyl-silanyloxymethyl]-butyl ester, octanoic acid 2-[{2-octanoyloxymethyl-2-[ethoxy-(3-mercapto-propyl)-ethoxy-silanyloxymethyl]-butoxy}-(3-octanoylsulfanyl-propyl)-methyl-silanyloxymethyl]-2-[(3-octanoylsulfanyl-propyl)-diethoxy-silanyloxymethyl]-butyl ester, acetic acid 2,2-bis-[(3-acetylsulfanyl-propyl)-(2,2-bis-hydroxymethyl-butoxy)-methyl-silanyloxymethyl]-butyl ester, acetic acid 2,2-bis-[(3-acetylsulfanyl-propyl)-(2,2-bis-hydroxymethyl-butoxy)-ethoxy-silanyloxymethyl]-butyl ester, octanoic acid 2-[(3-octanoylsulfanyl-propyl)-(2,2-bis-hydroxymethyl-butoxy)-ethyl-silanyloxymethyl]-2-[(2,2-bis-hydroxymethyl-butoxy)-(3-mercapto-propyl)-methyl-silanyloxymethyl]-butyl ester, octanoic acid 2-[(3-octanoylsulfanyl-propyl)-ethoxy-(2,2-bis-hydroxymethyl-butoxy)-silanyloxymethyl]-2-[(2,2-bis-hydroxymethyl-butoxy)-(3-mercapto-propyl)-ethoxy-silanyloxymethyl]-butyl ester, octanoic acid 2-[ethoxymethyl-(2,2-bis-octanoyloxymethyl-butoxy)-(3-octanonylsulfanyl-propyl)-silanyloxymethyl]-2-[(2,2-bis-aoctanoyloxymethyl-butoxy)-(3-mercapto-propyl)-ethoxy-silanyloxymethyl]-butyl ester, and combinations thereof.

The silanes of Formula (1) can also contain mercaptofunctional and monofunctional alkoxy groups. Mercaptofunctional silanes containing only monofunctional alkoxy groups can be used as reagents in the preparation of the silanes herein. However, it is understood that these monofunctional alkoxy groups can contribute to VOC emissions during use if the monofunctional alcohols that form upon hydrolysis of the silanes have a high enough vapor pressure at room temperature. Some examples of high boiling monofunctional alkoxy groups are those whose structures contain at least 12, and preferably 18,carbon atoms.

As previously indicated, the partial hydrolyzate(s) and/or condensate(s) of the cyclic and/or bridging mercaptofunctional silanes herein, i.e., cyclic and/or bridging dialkoxy mercaptofunctional and siloxanes and/or silanols, are also within the scope of the invention. These partial hydrolyzate(s) and/or condensate(s) can result as side products under many of the conditions of manufacture of the silanes herein and/or they can form upon storage, especially in humid conditions, or under conditions in which residual water remaining from their preparation is not completely removed subsequent to their preparation. If desired, the production of hydrolyzate(s) and/or condensate(s) can be reduced or minimized by suitable drying of the components making up the reaction media from which the silanes herein are produced and/or by drying the silane product(s). Procedures for drying the reactants and products include the use of dessicants and distillations using azeotropes of organic solvents and water, as are disclosed in: Purification of Laboratory Chemicals, Fifth edition, W. L. F. Armarego, Elsevier Science; 2003,the entire contents enclosed by reference.

When, however, in accordance with the invention it is desired to deliberately produce partial to substantially complete hydrolyzate(s) and/or condensate(s) of silane of Formula (1), i.e., products containing siloxane bonds, i.e., $Z^\beta = (—O—)_{0.5}$, such can be achieved by employing suitable stoichiometry or by using an excess of water in the manufacturing process described herein. Hydrolyzate(s) and siloxanes obtained from the silanes of the invention are represented by Formula (1) wherein $Z^\beta = (—O—)_{0.5}$ and/or X=OH are substantive (i.e., substantially larger than zero), for example, the molar ratio of $(—O—)_{0.5}$ to $[R^1A^1C(=O)A^2G^6(O—)_2]_{0.5}$ is from 1/100 to 1/1,more specifically from 1/50 to 1/2,and still more specifically from 1/25 to 1/5,and with the proviso that the silane of Formula (1) contains at least one $Z^{62}$ that is $[R^1A^1C(=O)A^2G^6(O—)_2]_{0.5}$ or at least one $Z^\theta$ that is $[R^1A^1C(=O)A^2G^6(O—)_2]$.

In one embodiment herein, the molar ratio of siloxane bridging groups, $(—O—)_{0.5}$, to dioxy bridging groups, $[R^1A^1C(=O)A^2G^6(O—)_2]_{0.5}$, is within a range of from 0/1 to 1/1,preferably from 0/1 to 0.2/1 and, more preferably, from 0.05/1 to 0.15/1.

In another embodiment herein, the sulfur-containing silanes herein, including their mixtures, can be loaded on a particulate carrier such as porous polymer, carbon black, a siliceous material such as silica, and the like, so that they are provided in solid form for addition to rubber in a rubber compounding operation.

In a further embodiment herein, sulfur-containing silanes of Formula (1) herein and mixtures thereof can be prepared by the general preparative process described herein for which there are numerous specific embodiments. Generally, in one embodiment, the process for making one or a mixture of silanes of Formula (1) involves a transesterification reaction between one or more alkoxysilanes of Formulae (2), (3), (4) and (5), one or more polyhydroxyl-containing compounds of Formulae (7), and optionally with one or more alcohols of Formulae (8) and/or (9).

In one embodiment, the process for preparing sulfur-containing silane of Formula (1) comprises:

a) mixing at least one sulfur-containing silane of general Formulae (2), (3), (4) and/or (5) with at least one diol having the structure $R^1A^1C(=O)A^2G^6(OH)_2$, optionally with alcohols of structures $[R^1A^1C(=O)A^2]_2G^6(OH)$ and/or $H-A^2G^6(OH)_2$, optionally in the presence of a transesterification catalyst;

b) transesterifying the mixture obtained from step (a0 with at least one diol having the structure $R^1A^1C(=O)A^2G^6(OH)_2$, optionally with alcohols of structures $[R^1A^1C(=O)A^2]_2G^6(OH)$ and/or $H-A^2G^6(OH)_2$, optionally in the presence of a transesterification catalyst; and, c) removing the X—H by-product(s) resulting from step (b); wherein each occurrence of X, $G^1$, $G^2$, $G^3$, $G^4$, $G^5$, $G^6$, $A^1$, $A^2$, $R^1$, $Y^1$, $Y^2$, $Y^3$, $Y^4$, $Y^5$ m, n, o, p, q, and r are defined herein and with the proviso that at least one of X is a hydrolyzable group.

The transesterifying reaction can be carried out by reacting a mixture of at least one silane of Formulae (2) to (6) with at least one hydroxyl-containing compound of Formula (7) and, optionally, at least one compound of Formulae (8) and/or (9) at a molar ratio of from 0.1 to 3.0, advantageously from 1.0 to 2.5, and still more advantageously from 1.5 to 2.0, moles of dihydoxyl- containing compound of Formula (7) per mole of silyl group and, optionally, from 0.1 to 3.0 moles each of hydroxyl-containing compound(s) of Formulae (8) and/or (9) per mole of silyl group to be transesterified.

The transesterifying reaction can be carried out within a fairly broad range of reaction conditions, e.g., at a temperature ranging from 0 to 200° C., specifically from 25° C. to 150° C. and more specifically from 60° C. to 80° C., while maintaining pressures on the order of from 0.1 to 2000 mm Hg absolute. In one embodiment, the temperature can range from 30° C. to 90° C., and the pressure can range from 1 to 80 mm Hg absolute. As those skilled in the art will recognize, excess diol Formula (7) and/or monoalcohol of Formula (8) can be utilized to increase reaction rate, and reduce the viscosity of the final product(s). In another embodiment, the reaction can be carried out by slowly adding diol of Formula (7) at the desired reaction temperature and vacuum to at least one silane of Formulae (2) to (6) or mixture thereof In yet another embodiment, as the lower boiling X—H by-product(s), e.g., monoalcohol, forms, it can be removed from the reaction mixture by a distillation cycle further driving the reaction to completion. As previously stated, the transesterifying reactions, if desired, can be catalyzed using one or more transesterification catalysts. Suitable tranesterification catalysts include strong protic acids, e.g., those whose $pK_a$ values are below 5.0, and transition metal complexes such as complexes of tin, iron, titanium and other metal catalysts. Catalysts suitable for the transesterifying reaction are disclosed in, e.g., "The Siloxane Bond, Physical Properties and Chemical Transformations", M. G. Voronkov, V. P. Mileshkevich and Yu. A. Yuzhelevskii, Consultants Bureau, a division of Plenum Publishing Company, New York (1978), Chapter 5, and is incorporated by reference herein in its entirety. Strong bases are generally unsuitable as transesterification catalysts since they react with the mercaptofunctional group and promote the reaction of the sulfur-containing functional group with the diol and result in the formation of mercaptides and/or sulfides. In one embodiment, the acid or metal catalysts can be used at a range of from 10 ppm to 2 weight percent, specifically from 20 ppm to 1000 ppm and, more specifically, from 100 ppm to 500 ppm In a further embodiment herein, the final mixture can optionally be buffered after the reaction is complete employing known and conventional procedures. Buffering the mixture will neutralize its content of strong protic acids and thus making the mixture less corrosive to metals and increasing its long-term storage stability.

In one specific embodiment, the products of the transesterification of silane of Formulae (2), (3), (4) (5) and/or (6) can comprise a considerable fraction of monomeric material in addition to the formation of dimers and other cyclic and/or bridged oligomers as illustrated by low viscosity reaction products. In one specific embodiment, the fraction of monomeric material can range from 1 to 99, more specifically from 10 to 50, and still more specifically, from 15 to 25 mole percent.

The process for making the silane compositions herein can optionally employ one or more inert solvents. Solvent can serve as diluent, carrier, stabilizer, refluxing aid and/or heating agent. Generally, any inert solvent that does not enter into the reaction or otherwise adversely affect the preparative process can be used. Suitable solvents are liquid under normal conditions and generally have boiling points below 150° C. Some non-limiting examples of suitable solvents include aromatic and aliphatic hydrocarbons, ethers, aprotic or chlorinated hydrocarbon solvents such as toluene, xylene, hexane, butane, diethyl ether, dimethylformamide, dimethyl sulfoxide, carbon tetrachloride and methylene chloride, and combinations thereof.

If desired, transesterifying can be conducted as a continuous operation which comprises:

a) reacting, in a thin film reactor, a thin film reaction medium comprising a mixture of at least one silane of Formulae (2), (3), (4) (5) and/or (6) with at least one dihydroxyl-containing compound of Formula (7), optionally, of Formulae (8) and/or (9), and, optionally, a transesterification catalyst, to provide silane(s) containing a cyclic and/or bridged dialkoxy group, and by-product monoalcohol;

b) vaporizing by-product monoalcohol from the thin film to drive the reaction;

c) optionally, recovering by-product monoalcohol, e.g., by condensation;

d) recovering silane reaction product(s); and, e) optionally, neutralizing the reaction medium to increase the storage stability of the silane product(s) therein.

The molar ratio of dihydroxyl-containing compound(s) to the mixture of silanes used in the continuous thin film process will depend upon the number of alkoxy groups that are desired to be replaced with a polyhydroxy-containing group, such as the non-limiting example of a diol. Theoretically, a molar ratio of 1.5 mole of diol of Formula (7) is required per mole of silyl group to be transesterified to replace all of the monoalkoxy or other hydrolyzable X— groups. A molar ratio of from 0.5 to 1.0 moles of diol can be used per mole of silyl group. In many cases, additional diol is desirable because in some cases only one of the hydroxyl groups of the diol reacts with a silyl group. Diols that react only once with a silyl group are defined as X in Formulae (2) to (6). The diols, referred to herein as "hydroxyalkoxy", reduce the viscosity and inhibit the gelation of the product silane(s). If desired, excess diol can be utilized to increase the reaction rate.

The method of forming the film can be any of those known in the art. Typical known devices include but are not limited to, falling film and wiped film evaporators. The minimum film thickness and flow rates will depend on the minimum wetting rate for the film-forming surface. The maximum film thickness and flow rates will depend on the flooding point for a particular film and particular reaction device. The alcohol is vaporized from the film by heating the film, by reducing pressure over the film, or by a combination of the conditions. Mild heating and reduced pressure are utilized to form the products described herein. Optimal temperatures and pressures (partial vacuum) for running the processes described will depend upon a specific silane's alkoxy or X groups and the diol used in the process. Additionally, if an optional inert solvent is used in the process, that choice will affect the optimal temperatures and pressures (partial vacuum) utilized. Some non-limiting examples of such solvents include those listed above. The by-product X—H, such as a monofunctional alcohol, that is vaporized from the film is removed from the reactive distillation device by a standard partial vacuum-forming device and can be condensed, collected and recycled as feed to other processes. The silane product(s), of Formula (1), is recovered by standard means from the reactive distillation device as a liquid phase. If an inert solvent has been used or if additional purification is desired, the silane product(s) can be fed to another similar distillation device or distillation column to effect that separation. Optionally, the transesterified reaction products can be neutralized to improve product storage.

If a protic catalyst is used to promote the transesterification of the silanes with diol, it can be useful to neutralize the catalyst with a base to improve the product's stability; however, only a stoichiometric amount of base is required to neutralize the protic catalyst; larger amounts of base will promote undesirable side reactions.

In another embodiment, a free-flowing filler particulate composition is provided which comprises:

a) at least one particulate filler; and, b) at least one silane of Formula (1) in admixture with and/or chemically bonded to particulate filler (a).

In another embodiment herein, there are provided various articles of manufacture, e.g., tires, industrial goods, shoe soles, hoses, seals, gaskets and cable jackets, in which at least one component is a rubber composition as described herein. The silanes and/or silane mixtures herein offer a means for significantly reducing volatile organic compound (VOC) emissions during rubber manufacture, increasing the dispersion of the filler within the rubber, improving the coupling between the organic polymers and fillers and reducing the amount of oil utilized in the rubber formulation.

In another embodiment herein, silane(s) of Formula (1) are useful as coupling agents between elastomeric resins (i.e., rubbers) and fillers. The sulfur-containing silane compositions are unique in that the high efficiency of the mercaptan and/or blocked mercaptan group can be utilized without the detrimental side effects typically associated with the use of mercaptosilanes, such as high processing viscosity, less than desirable filler dispersion, premature curing (scorch), and odor. These benefits are obtained because the mercaptan group is part of a high boiling compound that liberates diol or hydroxyl-containing compound upon use. During this non-productive mixing step, the cyclic and/or bridged alkoxysilyl groups can react with the filler. The sulfur-containing silane composition, free-flowing filler composition and rubber composition can be cured as described herein and/or using procedures known to those skilled in the art.

The sulfur-containing silane-based compositions herein provide significant advantages over traditional coupling agents that have found extensive use in the rubber and tire industries. These traditional silanes usually contain in their molecular structures three alkoxy groups, e.g., ethoxy groups, on each silicon atom, which results in the release of up to three moles of monohydroxy alcohol, e.g., ethanol, for each silane equivalent during the rubber manufacturing process in which the silane couples to the filler. This release of monoalcohols is undesirable because the monoalcohols are flammable and thus posing an elevated risk of fire, because they may form microporosity within cured rubber article and because they contribute so greatly to volatile organic compound (VOC) emissions that may be potentially harmful to the environment.

Utilizing any of the sulfur-containing silanes and/or silane mixtures disclosed herein can result in significantly reduced VOC emissions. The VOC emissions from a product/composition comprising the silanes of this invention can be considerably less than the VOC emissions resulting from other kinds of silanes. In yet a further embodiment, reduced VOC emissions can comprise less than 10, specifically less than 5 and, more specifically, less than 1, weight percent of the sulfur-containing silane. The VOC emissions are reduced because the resulting byproducts of hydrolysis are $R^1A^1C(=O)A^2G^6(OH)_2$, and optionally $[R^1A^1C(=O)A^2]_2G^6(OH)$ and/or $H-A^2G^6(OH)_2$, have a fairly high boiling point. Thus, e.g., the by-products of hydrolysis $R^1A^1C(=O)A^2G^6(OH)_2$ and, optionally, $[R^1A^1C(=O)A^2]_2G^6(OH)$ and/or $H-A^2G^6(OH)_2$, have boiling points typically greater than 260° C. at atmospheric pressure, more specifically, 300° C. at atmospheric pressure and, most specifically, 340° C. at atmospheric pressure, which results in less than 20 percent weight loss of the by-product, as measured by Environmental Protection Agency Method 24, specifically, less than 10 percent weight loss of the by-product as measured by this method and, more specifically, less than 1 percent weight loss as measured by this method.

In one embodiment, the by-products of hydrolysis $R^1A^1C(=O)A^2G^6(OH)_2$, and, optionally $[R^1A^1C(=O)A^2]_2G^6(OH)$ and/or $H-A^2G^6(OH)_2$, have initial boiling points generally greater than 250° C. at an atmospheric pressure of 101.3 kPa. These by-products are in compliance with European Union 'Paint Directive" 2004/42/EC for an organic compound that is not a volatile organic compound.

The sulfur-containing silane-based compositions described herein eliminate or greatly mitigate the foregoing problems by reducing volatile monoalcohol emissions to only one, less than one, and even essentially zero, moles of monoalcohol per silane equivalent. They accomplish this because the silane alkoxy groups are replaced with dihydroxyl-containing alcohols of Formula (7), and thus such compounds are released during the rubber manufacture process in place of much, or nearly all, of the monoalcohol released. The sulfur-containing silanes herein generally have boiling points in excess of typical rubber processing temperatures, are not vaporized out of the rubber during the rubber manufacture process, as is the case, e.g., with ethanol, but are retained by the rubber where they migrate to the silica surface due to their polarity and become hydrogen-bonded to the surfaces of siliceous fillers such as silicas or remained dissolved in the rubber matrix where they can function as plasticizer. The presence of hydroxyl-containing compounds on silica surfaces leads to further advantages not obtainable with ethanol (due to its volatility and ejection during the rubber compounding process) in the subsequent cure process, in which such presence prevents the silica surface from binding the curatives and thereby interfering with the cure. Traditional silanes not based on diols require more curative to counter losses due to silica binding.

The addition of hydroxyl-containing compounds to the rubber compounding formulation prior to and/or concurrent with the addition of curatives is of advantage for the efficient utilization of the curatives and polar substances such as, amines, amides, sulfenamides, thiurams, and guanidines. Whether hydroxyl-containing compounds are exclusively added as part of the silanes of Formula (1) or as free hydroxyl-containing compounds in combination with the silane coupling agents, these compounds are beneficial to the rubber compounding process. Their functions include dispersion of the free-flowing filler composition and acceleration, or retardation, of the curing reactions. The hydroxyl-containing compounds enhance the function of the curatives by interfering with their tendency to bind to the silica surface thereby forcing them into the rubber matrix to perform their function.

In one embodiment herein, there is provided a curable rubber composition comprising (a) at least one rubber component, (b) at least one particulate filler and (c) at least one sulfur-containing silane as described herein, and the cured rubber composition obtained therefrom.

An important advantage of the silanes described herein is that the by-products of the silane coupling process are themselves of utility in enhancing the rubber compounding process, the value of the resulting rubber compositions, and/or articles of manufacture employing the rubber compositions.

In one embodiment, at least one of the sulfur-containing silane coupling agents of Formula (1) is mixed with the organic polymer before, during, or after the compounding of the filler therein. The silane or silane mixture is added before and/or during the compounding of the filler into the organic polymer because these silanes facilitate and improve the dispersion of the filler. The total amount of silane present in the resulting rubber composition can range from 0.05 to 25, specifically, from 0.2 to 10 phr and, more specifically, from 3 to 8, parts by weight per hundred (phr) parts by weight of organic polymer.

The amount of sulfur-containing silane present in the free-flowing filler composition can range from 0.1 to about 70 weight, and more specifically, from about 0.5 to 20, weight percent based on total weight of free-flowing filler composition. The amount of filler in the free-flowing filler composition can range from 99.9 to 30, and more specifically, from 99.5 to 80, weight percent based on the total weight of free-flowing filler composition. The fillers can be used in quantities ranging from 5 to 100, more specifically from 25 to 80, and most specifically from 50 to 70 phr.

Sulfur-vulcanized rubber products are typically prepared by thermomechanically mixing rubber and various ingredients in a sequentially step-wise manner followed by shaping and curing the compounded rubber to form a vulcanized product. For the aforesaid mixing of the rubber and various ingredients, typically exclusive of sulfur and sulfur vulcanization accelerators (collectively "curing agents"), the rubber(s) and various rubber compounding ingredients are usually blended in at least one, and optionally (in the case of silica filled low rolling resistance tires) two or more, preparatory thermomechanical mixing stage(s) in suitable mixers. Such preparatory mixing is referred to as non-productive mixing or non-productive mixing steps or stages. Such preparatory mixing is usually conducted at temperatures of from 60 to 180, and, more specifically, from 140 to 160,° C.

Subsequent to the aforedescribed non-productive, or preparatory, mix stage(s), in a final mixing stage or stages, sometimes referred to as a productive mix stage, curing agents and possibly one or more additional ingredients are mixed with the rubber compound or composition, typically at a temperature of from 50° C. to 130° C., which is a lower temperature than those typically utilized in the preparatory mix stage(s), in order to prevent or retard premature curing (scorching) of the sulfur-curable rubber.

The rubber compound or composition may be allowed to cool, e.g., to 50° C. or even lower, sometimes after and/or during a process of intermediate mill mixing carried out between the aforesaid various mixing steps.

When it is desired to mold and to cure the rubber, the rubber containing the curatives is introduced into an appropriate mold and heated to at least 130° C. and up to 200° C. whereby vulcanization of the rubber by the sulfur-containing silane(s) and any other free sulfur source(s) in the rubber mixture is achieved.

By thermomechanical mixing, it is meant that the rubber compound, or composition of rubber and rubber compounding ingredients, is mixed in a rubber mixture under medium to high shear conditions as a result of which it autogenously heats up, primarily as a result of shear and associated friction within the rubber mixture, in the rubber mixer. Several chemical reactions can occur at various steps in the mixing and curing processes.

The first reaction of these reactions is a relatively fast reaction and is considered herein to take place between the filler and the hydrolyzable silyl group of the sulfur-containing silane of Formula (1). Such reaction can occur at a relatively low temperature, e.g., at 120° C. The second of the reactions is considered herein to be the reaction which takes place between the sulfur-containing portion of the silane and the sulfur-vulcanizable rubber component(s) at a higher temperature, e.g., above 140° C.

Other sulfur sources can be used, e.g., in the form of elemental sulfur as $S_8$. A sulfur donor is considered herein to be a sulfur-containing compound that liberates free, or elemental sulfur, at a temperature within a range of from 140° C. to about 200° C. Such sulfur donors include polysulfide vulcanization accelerators with at least two connecting sulfur atoms in their polysulfide bridge. The amount of free sulfur source added to the mixture can be controlled or manipulated as a matter of choice relatively independently from the addition of the sulfur-containing silane(s) of Formula (1). Thus, the independent addition of a sulfur source can be manipulated by the amount of addition thereof and by sequence of addition relative to the addition of other ingredients to the rubber mixture.

In another embodiment of the invention herein, a curable rubber composition is prepared by the process which comprises:

a) thermomechanically mixing, in at least one preparatory mixing operation, to a first elevated temperature, e.g., from 120° C. to 180° C., for a suitable period of time, e.g., a total mixing time of from 1 to 20 minutes:

i) 100 parts by weight of at least one sulfur-vulcanizable rubber selected from the group consisting of conjugated diene homopolymers and copolymers and copolymers of at least one conjugated diene and aromatic vinyl compound, ii) from 5 to 100 parts by weight of at least one particulate filler, e.g., one containing from 0 to 85 weight percent carbon black, and iii) from 0.05 to 20 parts by weight filler of at least one sulfur-containing silane of Formula (1);

b) blending the mixture from step (a), in a final thermomechanical mixing step at a second elevated temperature, e.g., from 50° C. to 130° C. for a period of time sufficient to blend the rubber, with from 0 to 5 parts by weight of at least one curing agent; and, (c) optionally, curing said mixture at a third elevated temperature of from 130° C. to 200° C., for a suitable period of time, e.g., from 5 to 60 minutes.

Rubber component (a) (organic polymers) and fillers are well known in the art and are described in numerous texts, of which two examples include The Vanderbilt Rubber Handbook; R. F. Ohm, ed.; R.T. Vanderbilt Company, Inc., Norwalk, Conn.; 1990 and Manual For The Rubber Industry; T. Kempermann, S. Koch, J. Sumner, eds.; Bayer AG, Leverkusen, Germany; 1993. In yet an even further embodiment, some representative non-limiting examples of suitable rubber component (a) (organic polymers) include solution styrene-butadiene rubber (SSBR), emulsion styrene-butadiene rubber (ESBR), natural rubber (NR), polybutadiene (BR), ethylene-propylene terpolymers (EPDM), and acrylonitrile-butadiene rubber (NBR).

Rubber component (a) is comprised of at least one diene-based elastomer, or rubber. Suitable monomers for preparing the rubbers are conjugated dienes which are those such as the non-limiting examples of isoprene and 1,3-butadiene; and suitable vinyl aromatic compounds which are those such as the non-limiting examples of styrene and alpha methyl styrene; and combinations thereof. The rubber is a sulfur curable rubber. Such diene based elastomer, or rubber, can be selected, e.g., from the non-limiting examples of at least one of cis-1,4-polyisoprene rubber (natural and/or synthetic), and preferably natural rubber), emulsion polymerization prepared styrene/butadiene copolymer rubber, organic solution polymerization prepared styrene/butadiene rubber, 3,4-polyisoprene rubber, isoprene/butadiene rubber, styrene/isoprene/butadiene terpolymer rubber, cis-1,4-polybutadiene, medium vinyl polybutadiene rubber (35-50 percent vinyl), high vinyl polybutadiene rubber (50-75 percent vinyl), styrene/isoprene copolymers, emulsion polymerization prepared styrene/butadiene/acrylonitrile terpolymer rubber and butadiene/acrylonitrile copolymer rubber. An emulsion polymerization derived styrene/butadiene (ESBR) is also contemplated as diene based rubbers for use herein such as those having a relatively conventional styrene content of 20 to 28 percent bound styrene or, for some applications, an ESBR having a medium to relatively high bound styrene content, namely, a bound styrene content of 30 to 45 percent. Emulsion polymerization prepared styrene/butadiene/acrylonitrile terpolymer rubbers containing 2 to 40 weight percent bound acrylonitrile in the terpolymer are also contemplated as diene based rubbers for use herein.

The solution polymerization prepared SBR (SSBR) typically has a bound styrene content within a range of from 5 to 50, more specifically from 9 to 36, and most specifically from 20 to 30, weight percent. Polybutadiene elastomer can he conveniently characterized, e.g., as having at least a 90 weight percent cis-1,4-content.

Examples of suitable filler materials include metal oxides such as silica (pyrogenic and precipitated), titanium dioxide, aluminosilicate, alumina, siliceous materials, such as clays and talc, and carbon black. Particulate, precipitated silica can also be used, particularly in connection with a silane. The filler can be a silica or a silica in combination with one or more other fillers. In some cases, a combination of silica and carbon black is utilized for reinforcing fillers for various rubber products including treads for tires. Alumina can be used either alone or in combination with silica. The term "alumina" refers to aluminum oxide, or $Al_2O_3$. In a further specific embodiment, the fillers can be hydrated or in anhydrous form. Use of alumina in rubber compositions is known, e.g., from U.S. Pat. No. 5,116,886 and EP 631 982, the entire contents of which are incorporated by reference herein.

In one embodiment of the invention, there is provided a process for preparing a rubber composition comprising adding to a rubber composition reaction-forming mixture, such as a mixture of the herein described rubber composition components (a), (b) and (c), an effective amount of at least one sulfur-containing silane compound of Formula (1), e.g., from 0.2 to 20, more specifically from 0.5 to 15 and most specifically of from 2 to 10 weight percent of sulfur-containing silane based on the total weight of rubber composition reaction-forming mixture. The rubber-forming mixture further includes a filler as described herein, e.g., in an amount of from 2 to 70, more specifically from 5 to 50, and most specifically from 20 to 40, weight percent thereof The rubber-forming mixture can further contain a rubber component(s) (a) described herein in a total amount of from 30 to 98, more specifically from 50 to 95, and most specifically from 60 to 80, weight percent thereof.

The sulfur-containing silane can be premixed, or pre-reacted, with the filler particles or added to the rubber mix during the rubber and filler processing, or mixing, stage. If the silane and filler are added separately to the rubber mixture during the rubber and filler mixing, or processing, stage it is considered that the sulfur-containing silane then couples in situ to the filler.

The vulcanized rubber composition should contain a sufficient amount of filler to contribute a reasonably high modulus and high resistance to tear. The combined weight of the filler can be as low as 5 to 100 phr, more specifically from 25 to 85 phr and most specifically from 50 to 70 phr.

Fillers of the present invention can be used as carriers for liquid silanes and reinforcing fillers for elastomers in which the sulfur-containing silane of Formula (1) is capable of reacting or bonding with the surface. The fillers that are used as carriers should be non-reactive with the sulfur-containing silane of this invention. The non-reactive nature of the fillers is demonstrated by the ability of the sulfur-containing silane to be extracted at greater than 50 weight percent of the loaded silane using an organic extraction solvent. The extraction procedure is disclosed in U.S. Pat. No. 6,005,027 the entire contents of which are incorporated by reference herein. Carriers include, but are not limited to, porous organic polymers, carbon black, diatomaceous earth and silicas characterized by the relatively low differential of less than 1.3 between the infrared absorbance at $3502\ cm^{-2}$ of the silica when taken at 105° C. and when taken at 500° C., as described in aforesaid U.S. Pat. No. 6,005,027. The amount of sulfur-containing silane of the present invention that can be loaded onto the carrier can range from 0.1 to 70 and more specifically, from 10 to 50, weight percent.

Suitable reinforcing fillers include those having surfaces that are reactive with silanes. Examples of such fillers include siliceous fillers, metal oxides such as silica (pyrogenic and/or precipitated), titanium, aluminosilicate and alumina, clays and talc, and the like. Particulate, precipitated silica processing reactive surface silanol groups is particularly useful for this purpose. A combination of from 0.1 to 20, more specifically from 0.5 to 10, weight percent of silane of Formula (1), and from 80 to 99.9,more specifically from 90 to 99.5,weight percent silica or other reinforcing filler is useful for reinforcing various rubber products, including treads for tires.

Precipitated silica when utilized as filler herein can be characterized as having a BET surface area, as measured using nitrogen gas, specifically in the range of from 40 to 600 $m^2/g$, more specifically from 50 to 300 $m^2/g$ and most specifically from 100 to 150, $m^2/g$. The BET method of measuring surface area is described in the Journal of the American Chemical Society, Volume 60,page 304 (1930) and is the method used herein. The silica typically can also be characterized by having a dibutylphthalate (DBP) absorption value of from 100 to 350,more specifically from 150 to 300 and most specifically from 200 to 250. Further, useful silica fillers, as well as the aforesaid alumina and aluminosilicate fillers, can be expected to have a CTAB surface area of from 100 to 220 $m^2/g$. The CTAB surface area is the external surface area as evaluated by cetyl trimethylammonium bromide with a pH of 9; the method is described in ASTM D 3849.

Mercury porosity surface area is the specific surface area determined by mercury porosimetry. In this technique, mercury is introduced into, and penetrates the pores of a sample after a thermal treatment to remove volatiles. Set-up conditions use a 100 mg sample; remove volatiles during 2 hours at 105° C. and ambient atmospheric pressure; and ambient to 2000 bars pressure measuring range. Such measurement can be performed according to the method described in Winslow, et al. in ASTM bulletin, p. 39 (1959) or according to DIN 66133. For the measurement, a CARLO-ERBA Porosimeter 2000 can be used. The average mercury porosity specific surface area for the selected silica filler should be in a range of from 100 to 300,more specifically from 150 to 275, and, most specifically, from 200 to 250 $m^2/g$.

A suitable pore size distribution for the silica, alumina and aluminosilicate according to such mercury porosity measurement is considered herein to be: five percent or less of its pores have a diameter of less than 10 nm; from 60 to 90 percent of its pores have a diameter of from 10 to 100 nm; from 10 to 30 percent of its pores have a diameter of from 100 to 1,000 nm; and from 5 to 20 percent of its pores have a diameter of greater than about 1,000 nm. The silica can be expected to have an average ultimate particle size, e.g., in the range of from 0.01 to 0.05 μm as determined by electron microscopy, although some or all of the silica particles can be even smaller, and in some cases larger, in size. Various commercially available silicas can be used herein, e.g., those available from PPG Industries under the HI-SIL trademark, in particular, HI-SIL 210, and 243; silicas available from Rhone-Poulenc, e.g., ZEOSIL 1165MP; silicas available from Degussa, e.g., VN2 and VN3,etc., and silicas available from Huber, e.g., HUBERSIL 8745.

Where it is desired for a rubber composition which contains both a siliceous filler such as silica, alumina and/or an aluminosilicate and a carbon black reinforcing pigment, to be primarily reinforced with siliceous filler(s) as the reinforcing pigment, it is often desired that the weight ratio of siliceous filler to carbon black be at least 3/1 and preferably at least 10/1 and, thus, in a range of from 3/1 to 30/1. More specifically, the filler can comprise from 15 to 95 weight percent precipitated silica, alumina and/or aluminosilicate and, correspondingly, from 5 to 85 weight percent carbon black having a CTAB value in a range of from 80 to 150. In one specific embodiment, alternatively, the filler can comprise from 60 to 95 weight percent of said silica, alumina and/or aluminosilicate and, correspondingly, from 40 to 5 weight percent carbon black. The siliceous filler and carbon black can be pre-blended or blended together in the manufacture of the vulcanized rubber.

The rubber composition herein can be compounded by methods known in the rubber compounding art, such as mixing the various sulfur-vulcanizable constituent rubbers with various commonly used additive materials as, for example, curing aids such as sulfur, activators, retarders and accelerators, processing additives such as oils, resins e.g., tackifying resins, silicas, plasticizers, fillers, pigments, fatty acid, zinc oxide, waxes, antioxidants and antiozonants, peptizing agents, and reinforcing materials such as, e.g., carbon black, and the like. Depending on the intended use of the sulfur-vulcanizable and sulfur-vulcanized material (rubbers), the additives mentioned herein are selected and commonly used in conventional amounts.

Vulcanization can be conducted in the presence of an additional sulfur vulcanizing agent. Some non-limiting examples of suitable sulfur vulcanizing agents include, e.g., elemental sulfur (free sulfur) or sulfur donating vulcanizing agents such as an amino disulfide, polymeric polysulfide or sulfur-olefin adducts, which are conventionally added in the final, i.e., productive, mixing step. The sulfur vulcanizing agents can be added in the productive mixing stage in an amount of from 0.4 to 3,or even in some circumstances, up to about 8,phr with a range of from 1.5 to 2.5,and in some cases from about 2 to about 2.4 phr, being suitable.

Vulcanization accelerators, i.e., additional sulfur donors, can also be used. It will be appreciated that accelerators can be those such as benzothiazole, alkyl thiuram disulfide, guanidine derivatives and thiocarbamates. Specific examples of such accelerators include mercapto benzothiazole, tetramethyl thiuram disulfide, benzothiazole disulfide, diphenylguanidine, zinc dithiocarbamate, alkylphenoldisulfide, zinc butyl xanthate, N-dicyclohexyl-2-benzothiazolesulfenamide, N-cyclohexyl-2-benzothiazolesulfenamide, N-oxydiethylenebenzothiazole-2-sulfenamide, N,N-diphenylthiourea, dithiocarbamylsulfenamide, N,N-diisopropylbenzothiozole-2-sulfenamide, zinc-2-mercaptotoluimidazole, dithiobis(N-methyl piperazine), dithiobis(N-beta-hydroxy ethyl piperazine), dithiobis(dibenzyl amine) and combinations thereof. Other additional sulfur donors, include, e.g., thiuram and morpholine derivatives, can be utilized. Representative of such donors are dimorpholine disulfide, dimorpholine tetrasulfide, tetramethyl thiuram tetrasulfide, benzothiazyl-2,N-dithiomorpholide, thioplasts, dipentamethylenethiuram hexasulfide, disulfidecaprolactam, and combinations thereof.

Accelerators are used to control the time and/or temperature required for vulcanization and to improve the properties of the vulcanizate. A single accelerator system can be used, i.e., a primary accelerator. Conventionally and more specifically, a primary accelerator(s) is used in total amounts ranging from 0.5 to 4,and preferably from 0.8 to 1.5 phr. Combinations of a primary and a secondary accelerator can be used with the secondary accelerator being used in smaller amounts (e.g., from 0.05 to 3 phr) in order to activate and to improve the properties of the vulcanizate. Delayed action accelerators and vulcanization retarders can also be used. Suitable accelerators include amines, disulfides, guanidines, thioureas, thiazoles, thiurams, sulfenamides, dithiocarbamates, xanthates and combinations thereof More specifically, the primary accelerator can be a sulfenamide. If a secondary accelerator is used, it can advantageously be a guanidine, dithiocarbamate or thiuram compound.

Tackifier resins, if used, can be incorporated at a level of from 0.5 to 10,and usually from 1 to 5,phr. Typical amounts of processing aids are from 1 to 50 and include aromatic, naphthenic and/or paraffinic processing oils, and combinations thereof. Typical amounts of antioxidants are from 1 to 5 phr and include diphenyl-p-phenylenediamine and those disclosed in the *Vanderbilt Rubber Handbook* (1978), pages 344-346. Typical amounts of antiozonants are from 1 to 5 phr. Typical amounts of fatty acids, if used, are from 0.5 to 3 phr and include stearic acid. Typical amounts of zinc oxide are from 2 to 5 phr. Waxes, e.g., microcystalline waxes, can typically be present at levels of from 1 to 5 phr. Typical amounts of peptizers are from 0.1 to 1 phr and include pentachlorothiophenol, dibenzamidodiphenyl disulfide and combinations thereof.

The rubber compositions herein can be used for various purposes, e.g., as soles, hoses, cable jackets, gaskets and other industrial goods. Such articles can be molded and cured by various known and conventional methods known to those skilled in the art. One particularly useful application of a rubber composition in accordance with the invention in the manufacture of tire treads. An advantage of tires, tire treads, or other articles of manufacture derived from the rubber composition herein is that they suffer from less VOC emissions during their lifetime and use as a result of having been manufactured from a rubber compound that contains less residual silane alkoxy groups than those rubber materials known and currently practiced in the art whose by-products of the silane hydrolysis reaction have high boiling points. This is a direct result of having used sulfur-containing coupling agents in their manufacture, which contain fewer or essentially no alkoxy groups on silicon relative to the blends of known and conventional silane coupling agents.

The invention can be better understood by reference to the following examples in which the parts and percentages are by weight unless otherwise indicated.

EXAMPLE 1

Trimethylolpropane (1037.5 grams, 7.7 moles), octanoic acid (557.5 grams, 3.9 moles), sodium hydrogen sulfate (purchased from Aldrich, 40.8 grams, 0.3 moles) and toluene (1500 mL) were charged into a 5-liter round-bottomed flask equipped with a mechanical stirrer, Dean-Stark trap and Friedrich condenser. The reaction mixture was heated to 115° C. for 5 hours. Water (78 mL) was collected. Toluene was stripped from the reaction product under atmospheric pressure to 150° C., and then cooled to 123° C. The reaction product was then sparged at 120 mm Hg for 1 hour at 120° C. followed by pressure filtration through a 20-micron pad. The weight of the product collected was 1530.7 grams. The reaction product, designated 1-A, was identified by gas chromagraphy/mass spectroscopy to be a mixture of mono, di and tri adducts of the octanoyl group on the trimethylolpropand starting reagent.

3-Mercaptopropyltriethoxysilane (Momentive Performance Products Silquest A-1891, 146.0 grams, 0.6 moles), octanoylthiopropyltriethoxysilane (Momentive Performance Products NXT silane, 521.1 grams, 1.4 moles) and reaction product A-1 (552.0 grams) were charged into a 1-liter round-bottomed flask equipped with a mechanical stirrer, distillation head and receiver flask. Sulfuric acid (0.61 grams) was added to the reaction flask and the mixture was heated to 60° C. under a vacuum of initially 220 mm Hg to 110 mm Hg for 1.5 hours. The reaction vessel was then sparged with nitrogen at 80° C. at 60 mm Hg for 2 hours. Ethanol (269.6 grams, 5.9 moles) was collected. The reaction product was neutralized with sodium ethoxide (21 wt. % in ethanol, 2.01 grams). The reaction vessel was sparged for 0.5 hours at 80° C. and 20 mm Hg. The weight of the product, designated 1-B, collected was 942.3 grams.

EXAMPLE 2

Trimethylolpropane (1037.5 grams, 7.7 moles), octanoic acid (557.5 grams, 3.9 moles), sodium hydrogen sulfate (purchased from Aldrich, 40.8 grams, 0.3 moles) and toluene (1500 mL) were charged into a 5-liter round-bottomed flask equipped with a mechanical stirrer, Dean-Stark trap and Friedrich condenser. The reaction mixture was heated to 115° C. for 5 hours. Water (78 mL) was collected. Toluene was stripped from the reaction product under atmospheric pressure to 150° C., and then cooled to 123° C. The reaction product was then sparged at 120 mm Hg for 1 hour at 120° C. The product was then pressure filtered through a 20-micron pad. The weight of the product collected was 1530.7 grams. The product (978.2 grams) was combined with 445 grams hexane. The mixture was washed three times with 500 grams of de-ionized water in a separatory funnel to remove trimethylolpropane. Hexane was stripped from the reaction mixture under atmospheric pressure at 106° C. Toluene (329.6 g) was added to the stripped product. Water was removed from the mixture using a Dean-Stark trap for 5 hours at 120° C. Toluene was then removed from the reaction product under a vacuum of 200 mm Hg to 0.305 mm Hg while gradually heating the reaction vessel from ambient temperature to 97° C. The weight of the product collected was 556.6 grams. The reaction product, designated 2-A, was identified by gas chromagraphy/mass spectroscopy to be a mixture of mono, di and tri adducts of the octanoyl group on the trimethylolpropane starting reagent.

3-Mercaptopropyltriethoxysilane (Silquest A-1891, 33.4 grams, 0.14 moles) and reaction product 2-A (125.2.0 grams) were charged into a 500-mL round-bottomed flask equipped with a magnetic stirrer, distillation head and receiver flask. Sulfuric acid (0.12 grams) was added to the reaction flask and the mixture was heated to 55° C. under a vacuum of initially 200 mm Hg to 0.2 mm Hg for 2 hours. Ethanol (19.6 grams, 0.43 moles) was collected. The reaction product was neutralized with sodium ethoxide (21 wt. % in ethanol, 0.40 grams). The reaction vessel was then heated for 0.5 hours at 80° C. and 0.1 mmHg. The weight of the product, designated 2-B, collected was 134.0 grams.

EXAMPLE 3

Trimethylolpropane (333.5 grams, 2.5 moles), triethylamine (311.2 grams, 3.1 moles) and methylene chloride (500 mL) were charged into a 3-liter round-bottomed flask equipped with a mechanical stirrer, addition funnel and Friedrich condenser. After heating the reaction flask to 50° C., ethyl hexanoyl chloride (428.8 grams, 2.6 moles) was slowly added to the reaction vessel over 5.5 hours. The reaction product was pressure filtered through a 0.5-micron pad. The filtrate was stripped of excess triethylamine and methylene chloride under atmospheric pressure at 150° C. and thereafter vacuum stripped at 0.5 mm Hg at 140° C. The product was then pressure filtered through a 20-micron pad. The weight of the product collected was 573.5 grams. The reaction product, designated 3-A, was identified by gas chromagraphy/mass spectroscopy to be a mixture of mono, di and tri adducts of the octanoyl group on the trimethylolpropane starting reagent.

3-Mercaptopropyltriethoxysilane (Silquest A-1891, 73.9 grams, 0.31 moles) and product 2-B (185.5 grams) were charged into a 500-mL round-bottomed flask equipped with a magnetic stirrer, distillation head and receiver flask. The reaction flask was heated at 50° C. Sulfuric acid (0.66 grams) was charged into the flask. The reaction vessel was then heated at 50° C. to 80° C. under a vacuum of initially 220 mm Hg to 0.1 mm Hg over 2.5 hours. Ethanol (40.6 grams, 0.88 moles) was collected. The reaction product was neutralized with 2.07 grams of sodium ethoxide solution (21 wt. % in ethanol.) Ethanol was removed from the reaction product at 80° C. under a vacuum of 0.1 mm Hg. The weight of the product, designated 3-B, collected was 216.4 grams.

EXAMPLE 4

Trimethylolpropane (391.0 grams, 2.9 moles), triethylamine (339.2 grams, 3.6 moles) and methylene chloride (550 mL) were charged into a 3-liter round-bottomed flask equipped with a mechanical stirrer, addition funnel and Friedrich condenser. After heating the reaction flask to 50° C., hexanoyl chloride (392.5 grams, 2.9 moles) was slowly added to the reaction vessel over 5 hours. The reaction product was pressure filtered through a 3.5-micron pad. The filtrate was stripped of excess triethylamine and methylene chloride under atmospheric pressure at 140° C. and thereafter vacuum stripped at 0.5 mm Hg at 147° C. The product was then pressure filtered through a 20-micron pad. The weight of the product, designated 4-A, collected was 545.6 grams.

3-Mercaptopropyltriethoxysilane (Silquest A-1891, 42.3 grams, 0.18 moles) and product 4-A from above (100.0 grams) were charged into a 500-mL round-bottomed flask equipped with a magnetic stirrer, distillation head and receiver flask. The reaction flask was heated to 65° C. Sulfuric acid (0.23 grams) was charged into the flask. The reaction vessel was then heated at 65° C. to 70° C. under a vacuum of initially 240 mm Hg to 0.2 mm Hg over 2 hours. Ethanol (23.2 grams, 0.50 grams) was collected. The reaction product was neutralized with 0.76 grams of sodium ethoxide solution (21 wt. % in ethanol). Ethanol was removed from the reaction product at 70° C. under a vacuum of 0.2 mmHg. The weight of the product, designated 4-B, collected was 111.5 grams.

EXAMPLE 5

Trimethylolpropane (441.9 grams, 3.3 moles), triethylamine (441.9 grams, 4.4 moles) and methylene chloride (200 mL) were charged into a 3-liter round-bottomed flask equipped with a mechanical stirrer, addition funnel and Friedrich condenser. After heating the reaction flask to 50° C., a mixture of valeryl chloride (397.1 grams, 3.3 moles) and methylene chloride (150 mL) was slowly added to the reaction vessel over 3.5 hours. The reaction product was pressure filtered through a 0.5-micron pad. The filtrate was stripped of excess triethylamine and methylene chloride under atmospheric pressure at 80° C. and thereafter vacuum stripped at 0.5 mm Hg at 140° C. The product was then pressure filtered through a 20-micron pad. The weight of the product, designated 5-A, collected was 530.2 grams.

3-Mercaptoproyltriethoxysilane (Silquest A-1891, 44.3 grams, 0.19 moles) and product 5-A, supra, (102.1 grams) were charged into a 500-mL round-bottomed flask equipped with a magnetic stirrer, distillation head and receiver flask. The reaction flask was heated to 50° C. Sulfuric acid (0.21 grams) was charged into the flask. The reaction vessel was then heated at 50° C. to 80° C. under a vacuum of initially 230 mm Hg to 0.1 mm Hg for 2.5 hours. Ethanol (24.1 grams, 0.52 moles) was collected. The reaction product was neutralized with 0.76 grams sodium ethoxide solution (21 wt. % in ethanol). Ethanol was removed from the reaction product at 80° C. under a vacuum of 0.1 mmHg. The weight of the product, designated 5-B, collected was 116.3 grams.

EXAMPLE 6

Trimethylolpropane (659.8 grams, 4.9 moles), triethylamine (798.1 grams, 7.9 moles) and methylene chloride (700 mL) were charged into a 5-liter round-bottomed flask equipped with a mechanical stirrer, addition funnel and Friedrich condenser. After heating the reaction flask to 50° C., octanoyl chloride (960.23 grams, 5.9 moles) was slowly added to the reaction vessel over 7 hours. The reaction product was pressure filtered through a 0.1-micron pad and then through a 0.01-micron pad. The filtrate was stripped of excess triethylamine and methylene chloride under atmospheric pressure at 140° C., thereafter vacuum stripped at 0.5 mm Hg at 80° C. and then sparged with nitrogen for 8 hours at 80° C. at 40 mmHg. The product was pressure filtered through a 5-micron pad. The weight of the product, designated 6-A, collected was 1025.7 grams.

EXAMPLE 7

Trimethylolpropane (32.5 grams, 0.24 moles), dibutyltindilaurate (0.4 grams) and toluene (23.4 grams) were charged into a 250-mL round-bottomed flask equipped with a magnetic stirrer and addition funnel. After heating the reaction flask to 60° C., octylisocyanate (24.9 grams, 0.16 moles) was slowly added to the reaction vessel over one hour. Toluene was removed from the reaction product at 50° C. under 0.1 mm Hg. The weight of the product, designated 7-A, collected was 51.8 grams.

EXAMPLES 8 TO 15

The amount of volatile organic compound was determined for the mixture of trimethylolpropane and/or mono-, di- and tri-adducts of trimethylolpropane that were prepared in Examples 3 to 6 and the sulfur-containing silanes of Examples 1 to 4. The amount of VOC was determined using the method of the Environmental Protection Agency Method 24, the entire contents of which are incorporated herein by reference. The results are presented in Table 1.

TABLE 1

The non-volatile component of hydroxyl-containing compounds and sulfur-containing silanes defined herein, as determined by Method 24.

| Example | Reaction Product | Identity | Amount of non-volatile organic compound present, weight percent |
|---|---|---|---|
| 8 | 3A | Hydroxyl-containing compound | 90.0 |
| 9 | 4A | Hydroxyl-containing compound | 89.5 |
| 10 | 5-A | Hydroxyl-containing compound | 86.9 |
| 11 | 6-A | Hydroxyl-containing compound | 89.8 |
| 12 | 7-A | Hydroxy-containing compound | 93.2 |
| 13 | 2-B | Sulfur-containing silane | 97.8 |
| 14 | 3-B | Sulfur-containing silane | 94.2 |
| 15 | 4-B | Sulfur-containing silane | 93.7 |

The data in Table I show that both the hydrolysis products, the hydroxyl-containing compounds and the sulfur-containing silane herein generate less than 10 weight percent volatile organic compounds as measured by EPA Method 24.

COMPARATIVE EXAMPLE 16 AND EXAMPLES 17 AND 18

Cured rubber compositions in the form of plaques were prepared and their physical and dynamic properties measured. A typical silica-rubber SBR formulation was used as described below in Table 2 for making the test placques. Mixing was carried out in a 1.7-liter Banbury tangential mixer.

TABLE 2

Silica-containing Rubber Formulation

| PHR | Components |
|---|---|
| 103.2 | SSBR (Buna VSL 5025-1 from Bayer AG) |
| 25 | BR (Budene 1207 from Goodyear) |
| 80 | Silica (Zeosil 1165MP from Rhodia) |
| 3.0 | carbon black (N-330) |
| Variable | silane |
| 4.5 | oil (Sundex 8125 from Sun Oil) |
| 2.5 | zinc oxide (Kadox 720C from ZincCorp.) |
| 1.0 | stearic acid (Industrene R from Witco, Crompton) |
| 2.0 | N-(1,3-dimethylbutyl)-N'-phenyl-p-phenylenediamine, 6 PPD, (Flexzone 7P from Crompton) |
| 1.5 | Wax (Sunproof Improved from Uniroyal, Crompton) |
| | Final Mix Components |
| 1.4 | sulfur (Rubbermakers Sulfur 104 from Harwick) |
| 1.7 | N-cyclohexyl-2-benzothiazole sulfonamide, CBS, (Delac S from Crompton) |
| 2.0 | Diphenyl guanidine, DPG, (from Crompton) |

The procedure which was used for preparing the single non-productive mix is presented in Table 3 below.

TABLE 3

One-pass procedure (Cooling with water at 25° C., 68% fill factor)

| Step | Procedure |
|---|---|
| 1 | Add polymers, RDM (ram down mix) 30 seconds |
| 2 | Add 50% silica, all silane, RDM 30 seconds |
| 3 | Add remaining 50% silica, oil, RDM 30 seconds |
| 4 | Dust down, RDM 20 seconds |
| 5 | Add ZnO, steric acid, Flexzone 7P, wax and carbon black, RDM 60 seconds |
| 6 | Dust down, RDM to 170° C. (in approx. 2 minutes) by increasing rotor speed |
| 7 | Hold at 170° C. for 8 minutes by changing speeds on the mixer. |
| 8 | Dump, sheet off roll mill at 65-70° C. to cool |

The procedure for preparing the single productive mix involved adding sulfur and accelerators (primary and secondary) into a masterbatch prepared as described in Table 3 supra on a two-roll mill at 65 to 70° C. After all the silica filler, silane and oil were incorporated into the mix, the rpm of the rotors was raised so as to achieve the desired silanization temperature. The mix was then held at that temperature for 8 minutes. The mix procedures are presented in Table 2, above.

Curing and testing of the cured rubber plaques were carried out according to ASTM standards. In addition, small strain dynamic tests were carried out on a Rheometrics Dynamic Analyzer (ARES—Rheometrics Inc.). The specific curing procedure, measurements and measuring procedures were as follows:

| Curing Procedure/Measurement | Testing Standard |
|---|---|
| Mooney viscosity and scorch | ASTM D1646 |
| Oscillating disc rheometry | ASTM D2084 |
| Curing of test plaques | ASTM D3182 |
| Stress-strain properties | ASTM D412 |
| Heat build-up | ASTM D623 |

Dynamic Mechanical properties, Payne effect strain sweeps, were carried out from dynamic strain amplitudes of 0.01% to 25% shear strain amplitude at 10 Hz and 60° C. The dynamic parameters, $G'_{initial}$, $\Delta G'$, $G''_{max}$, $\tan \delta_{max}$ were extracted from the non-linear responses of the rubber compounds at small strains. In some cases, steady state values of tan δ were measured after 15 minutes of dynamic oscillations at strain amplitudes of 35% (at 60° C.). Temperature dependence of dynamic properties were also measured from about −80° C. to +80° C. at small strain amplitudes (1 or 2%) at a frequency of 10 Hz. The Theological, physical and dynamic properties of the rubber compounds, Comparative Example 16 (silane is bis-triethoxysilylpropyl tetrasulfide, Momentive Performance Materials Silquest* A-1289 silane) and Examples 17 and 18 (Silanes 2-B and 3-B) are given in Table 4

TABLE 4

The rheological, physical and dynamic properties of rubber

| | Example No. | | |
|---|---|---|---|
| | Comp. 16 | 17 | 18 |
| Silane loading phr | 7.0 | 4.0 | 4.0 |
| Number of non-productive passes | 2 | 1 | 1 |
| Temperature of thermal step, ° C. | 160 | 170 | 170 |
| Mooney Properties | | | |
| Viscosity at 100° C. (ML1 + 4) | 60.9 | 67.8 | 65.1 |
| Scorch at 135° C. (MS1 + t₃) (min) | 8.69 | 7.30 | 7.97 |
| Cure at 135° C. (MS1 + t₁₈) (min) | 11.63 | 10.09 | 11.27 |
| Rheometer (ODR) Properties, (1° arc at 149° C.) | | | |
| $M_L$ (dN-m) | 11.41 | 10.68 | 12.42 |
| $M_H$ (dN-m) (30 min. timer) | 34.08 | 30.82 | 33.42 |
| t90 (min) (30 min. timer) | 17.23 | 11.57 | 12.62 |
| $t_{s1}$ (min) | 4.64 | 4.32 | 4.35 |
| $M_H - M_L$ | 22.67 | 20.13 | 21.01 |
| Physical Properties, (cured t90 at 149° C.) | | | |
| Hardness (Shore A) | 58 | 56 | 60 |
| Tensile (MPa) | 19.55 | 20.03 | 19.30 |
| Elongation (%) | 382 | 394 | 367 |
| 25% Modulus (MPa) | 0.90 | 0.78 | 0.92 |
| 100% Modulus (MPa) | 2.28 | 1.90 | 2.18 |
| 300% Modulus (MPa) | 13.77 | 12.92 | 14.23 |
| Reinforcement Index, (300%/100%) | 6.03 | 6.80 | 6.53 |
| Abrasion Loss (DIN) (mm³) | 124.3 | 178.4 | 119.7 |
| Dynamic Properties, (cured t90 at 149° C.) Non-linearity (0-10%) 60° C. | | | |
| $G'_{initial}$ (MPa) | 3.77 | 2.77 | 4.00 |
| $\Delta G'$ (MPa) | 2.00 | 1.19 | 2.10 |
| $G''_{max}$ (MPa) | 0.42 | 0.31 | 0.43 |
| Tan $\delta_{max}$ | 0.14 | 0.14 | 0.15 |
| Temperature Dependence | | | |
| Tan δ at 0° C. | 0.47 | 0.48 | 0.53 |
| Tan δ at 60° C. | 0.13 | 0.13 | 0.13 |
| G' 0° C. (MPa) | 6.24 | 5.63 | 6.75 |
| G' 60° C. (MPa) | 2.32 | 2.06 | 2.35 |

While the invention has been described with reference to a number of exemplary embodiments, it will be understood by those skilled in the art that various changes can be made and equivalents can be substituted for elements thereof without departing from the scope of the invention. In addition, many modifications can be made to adapt a particular situation or material to the teachings of the invention without departing from essential scope thereof. Therefore, it is intended that the invention not be limited to any particular exemplary embodiment disclosed herein.

What is claimed is:

1. A sulfur-containing silane of general Formula (1):

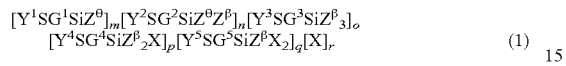

$$[Y^1SG^1SiZ^\theta]_m[Y^2SG^2SiZ^\theta Z^\beta]_n[Y^3SG^3SiZ^\beta_3]_o$$
$$[Y^4SG^4SiZ^\beta_2X]_p[Y^5SG^5SiZ^\beta X_2]_q[X]_r \quad (1)$$

wherein:

each occurrence of $G^1$, $G^2$, $G^3$, $G^4$ and $G^5$ is independently a hydrocarbylene group containing up to 15 carbon atoms selected from the group consisting of alkylene, alkenylene, arylene, and aralkylene groups;

each occurrence of X is independently selected from the group consisting of —R, —OR, —OC(=O)R$^3$, H-A$^2$G$^6$(OH)(O—), R$^1$A$^1$C(=O)A$^2$G$^6$(OH)O— and [R$^1$A$^1$C(=O)A$^2$]$_2$G$^6$O—, wherein each occurrence of A$^1$ is independently selected from the group consisting of a covalent chemical bond between R$^1$ and the carbonyl group, an oxygen atom and —NR$^2$—; each occurrence of A$^2$ is independently selected from a covalent chemical bond between G$^6$ and the carbonyl group, an oxygen atom and —NR$^2$—; each occurrence of R is independently selected from the group consisting of straight, cyclic and branched alkyl, alkenyl, aryl, and aralkyl groups containing up to 12 carbon atoms; each occurrence of R$^1$ is independently selected from the group consisting of hydrogen and straight, cyclic or branched alkyl, alkenyl, aryl, and aralkyl groups containing up to 18 carbon atoms; each occurrence of R$^2$ is independently selected from the group consisting of hydrogen and straight, cyclic or branched alkyl, alkenyl, aryl, and aralkyl groups containing up to 18 carbon atoms; each occurrence of R$^3$ is independently selected from the group consisting of hydrogen and straight, cyclic or branched alkyl, alkenyl groups, aryl groups, and aralkyl groups containing from 1 to 29 carbon atoms; and G$^6$ is independently a hydrocarbylene group of from 3 to 15 carbon atoms;

each occurrence of Y$^1$, Y$^2$, Y$^3$, Y$^4$, and Y$^5$ is independently selected from hydrogen and an acyl group, R$^3$C(=O)—, wherein each occurrence of R$^3$ is independently selected from the group consisting of hydrogen and straight, cyclic or branched alkyl, alkenyl, aryl, and aralkyl groups containing up to 30 carbon atoms;

each occurrence of Z$^\beta$, which forms a bridging structure between two silicon atoms, is selected from the group consisting of [R$^1$A$^1$C(=O)A$^2$G$^6$(O—)$_2$]$_{0.5}$ and [H-A$^2$G$^6$(O—)$_2$]$_{0.5}$, wherein each occurrence of A$^1$ is independently selected from the group consisting of a covalent chemical bond between R$^1$ and the carbonyl group, an oxygen atom and —NR$^2$; each occurrence of A$^2$ is independently selected from the group consisting of a covalent chemical bond between G$^6$ and the carbonyl group, oxygen atom and —NR$^2$—; each occurrence of R$^1$ is independently selected from the group consisting of hydrogen and straight, cyclic or branched alkyl, alkenyl, aryl, and aralkyl groups containing up to 18 carbon atoms; each R$^2$ is independently selected from the group consisting of hydrogen and straight, cyclic or branched alkyl, alkenyl, aryl, and aralkyl groups containing up to 18 carbon atoms; and each occurrence of G$^6$ is independently a hydrocarbylene group of from 3 to 15 carbon atoms;

each occurrence of Z$^\theta$, which forms a cyclic structure with a silicon atom, is independently selected from the group consisting of R$^1$A$^1$C(=O)A$^2$G$^6$(O—)$_2$ and H-A$^2$G$^6$(O—)$_2$, wherein each occurrence of A$^1$ is independently selected from the group consisting of a covalent chemical bond between R$^1$ and the carbonyl group, oxygen atom and —NR$^2$—; each occurrence of A$^2$ is independently selected from the group consisting of a covalent chemical bond between G$^6$ and the carbonyl group, oxygen atom and —NR$^2$—; each occurrence of R$^1$ is independently selected from the group consisting of hydrogen and straight, cyclic or branched alkyl groups, alkenyl groups, aryl groups, and aralkyl groups containing from 1 to 18 carbon atoms; each occurrence of R$^2$ is independently selected from the group consisting of hydrogen and straight, cyclic or branched alkyl groups, alkenyl groups, aryl groups, and aralkyl groups containing from 1 to 18 carbon atoms; and each occurrence of G$^6$ is independently a hydrocarbylene group of from 3 to 15 carbon atoms;

each occurrence of subscripts m, n, o, p, q and r independently is an integer wherein m is 0 or 1; n is 0 to 18; o is 0 to 20; and, p is 0 to 20; q is 0 to 20 and r is 0 or 1, with the provisos that, (i) when m is 1, r is 1 and n+o+p+q is 0, (ii) when m is 0, r is 0 and n+o+p+q is equal to or greater than 2, and (iii) the silane contain at least one Z$^\beta$ with the structure [R$^1$A$^1$C(=O)A$^2$G$^6$(O—)$_2$]$_{0.5}$ or at least one Z$^\theta$ of the structure R$^1$A$^1$C(=O)A$^2$G$^6$(O—)$_2$.

2. The sulfur-containing silane of claim 1 wherein:

each occurrence of G$^1$, G$^2$, G$^3$, G$^4$ and G$^5$ is independently a hydrocarbylene group containing a straight or branched chain alkylene group of from 1 to 6 carbon atoms; each occurrence of X is independently selected from the group consisting of —R, [R$^1$A$^1$C(=O)A$^2$]$_2$G$^6$O— and R$^1$A$^1$C(=O)A$^2$G$^6$(OH)O—, wherein each A$^1$ is a covalent bond between R$^1$ and the carbonyl group; each A$^2$ is an oxygen atom; each R is independently a straight chain alkyl group containing from 1 to 6 carbon atoms; each R$^1$ is independently an alkyl group containing from 2 to 12 carbon atoms; each R$^2$ is independently selected from the group consisting of hydrogen and an alkyl group containing from 1 to 6 carbon atoms; and G$^6$ is independently a trivalent alkylene group of from 3 to 6 carbon atoms considered as derived from an alkane;

each occurrence of Y$^1$, Y$^2$, Y$^3$, Y$^4$, and Y$^5$ is selected from hydrogen and an acyl group, R$^3$C(=O)—, wherein R$^3$ is an alkyl group of from 6 to 12 carbon atoms;

each occurrence of Z$^\beta$, which forms a bridging structure between two silicon atoms, is independently [R$^1$A$^1$C(=O)A$^2$G$^6$(O—)$_2$]$_{0.5}$, wherein each A$^1$ is independently selected from the group consisting of a covalent chemical bond between R$^1$ and the carbonyl group; each A$^2$ is an oxygen atom; each R$^1$ is independently an alkyl group containing from 2 to 12 carbon atoms; and each G$^6$ is independently a trivalent alkylene group of from 3 to 6 carbon atoms considered as derived from an alkane; and, each occurrence of Z$^\theta$, which forms a cyclic structure with a silicon atom, is independently R$^1$A$^1$C(=O)A$^2$G$^6$(O—)$_2$, wherein each A$^1$ is independently selected from the group consisting of a covalent chemical bond between $R^1$ and the carbonyl group; each $A^2$ is an oxygen atom; each $R^1$ is independently an alkyl group containing from 2 to 12 carbon atoms; and $G^6$ is independently a trivalent alkylene group of from 3 to 6 carbon atoms derived from an alkane.

3. The sulfur-containing silane of claim 2 wherein m is 1, r is 1 and n+o+p+q is 0.

4. The sulfur-containing silane of claim 3 wherein m is 0, r is 0 and n+o+p+q is equal to or greater than 2.

5. The sulfur-containing silane of claim 1 wherein X is $[R^1A^1C(=O)A^2]_2G^6O-$ and $R^1A^1C(=O)A^2G^6(OH)O-$, wherein each $A^1$ is a covalent bond between $R^1$ and the carbonyl group; each $A^2$ is an oxygen atom; each R is independently a straight chain alkyl group containing from 1 to 6 carbon atoms; each $R^1$ is independently an alkyl group containing from 2 to 12 carbon atoms; each $R^2$ is independently selected from the group consisting of a hydrogen and an alkyl group containing from 1 to 6 carbon atoms; and $G^6$ is independently a trivalent alkylene group of from 3 to 6 carbon atoms derived from an alkane.

6. The sulfur containing silane of claim 5 wherein $R^1$ is octyl and $G^6$ is $CH_3CH_2C(CH_2-)_3$.

7. The sulfur-containing silane of claim 1 wherein $Y^1$, $Y^2$, $Y^3$, $Y^4$ and $Y^5$ are hydrogen.

8. The sulfur-containing silane of claim 1 which is at least one silane selected from the group consisting of hexanoic acid 2-(3-butyrylsulfanyl-propyl)-5-ethyl-2-methyl-[1,3,2]dioxasilinan-5-yl ester, hexanoic acid 2-(3-butyrylsulfanyl-propyl)-5-ethyl-2-ethoxy-[1,3,2]dioxasilinan-5-yl ester, hexanoic acid 2-(3-butyrylsulfanyl-propyl)-2-(3-hexanoyloxy-4-hydroxy-propoxy)-[1,3,2]dioxasilinan-5-yl ester, octanoic acid 2-(3-hexanoyloxymethyl-4-hydroxy-3-methyl-propoxy)-2-(3-hexanoylsulfanyl-propyl)-5-methyl-[1,3,2]dioxasilinan-5-ylmethyl ester, octanoic acid 2-(3-hexanoyloxymethyl-4-hydroxy-3-methyl-propoxy)-2-(3-mercapto-propyl)-5-methyl-[1,3,2]dioxasilinan-5-ylmethyl ester, 2-ethyl-hexanoic acid 2-[3-(2-ethyl-hexanoyloxymethyl)-4-hydroxy-3-methyl-propoxy]-2-[3-(2-ethyl-hexanoylsulfanyl)-propyl]-5-methyl-[1,3,2]dioxasilinan-5-ylmethyl ester, 2-ethyl-hexanoic acid 2-[4-(2-ethyl-hexanoyloxy)-3-methyl-butoxy]-2-[3-(2-ethyl-hexanoylsulfanyl)-propyl]-5-methyl-[1,3,2]dioxasilinan-5-ylmethyl ester, octanoic acid 5-ethyl-2-(3-mercapto-propyl)-2-methyl-[1,3,2]dioxasilinan-5-yl ester, octanoic acid 2-ethoxy-5-ethyl-2-(3-mercapto-propyl)-[1,3,2]dioxasilinan-5-yl ester, octanoic acid 2-(2,2-bis-hydroxymethyl-butoxy)-5-ethyl-2-(3-mercapto-propyl)-[1,3,2]dioxasilinan-5-yl ester, octanoic acid 5-ethyl-2-(2-hydroxymethyl-2-octanoyloxymethyl-butoxy)-2-(3-mercapto-propyl)-[1,3,2]dioxasilinan-5-yl ester, octanoic acid 2-(2,2-bis-octanoyloxymethyl-butoxy)-5-ethyl-2-(3-mercapto-propyl)-[1,3,2]dioxasilinan-5-yl ester, octanoic acid 2-(2,2-bis-octanoyloxymethyl-butoxy)-5-ethyl-2-(3-octanoylsulfanyl-propyl)-[1,3,2]dioxasilinan-5-yl ester, octanoic acid 5-ethyl-2-(2-hydroxymethyl-2-octanoyloxymethyl-butoxy)-2-(3-octanoylsulfanyl-propyl)-[1,3,2]dioxasilinan-5-yl ester, octanoic acid 5-ethyl-2-{2-[5-ethyl-5-hydroxymethyl-2-(3-mercapto-propyl)-[1,3,2]dioxasilinan-2-yloxymethyl]-2-octanoyloxymethyl-butoxy}-2-(3-octanoylsulfanyl-propyl)-[1,3,2]dioxasilinan-5-yl ester, octanoic acid 5-ethyl-2-{2-[5-ethyl-5-octanoyloxymethyl-2-(3-octanoylsulfanyl-propyl)-[1,3,2]dioxasilinan-2-yloxymethyl]-2-octanoyloxymethyl-butoxy}-2-(3-octanoylsulfanyl-propyl)-[1,3,2]dioxasilinan-5-yl ester, Octanethioic acid 3-(5-ethyl-2-{2-ethyl-4-(3-ethyl-3-methyl-heptanoylamino)-2-(octanoylamino-methyl)-3-[2-(3-octanoylsulfanyl-propyl)-[1,3,2]dioxasilinan-2-yloxy]-butoxy}-5-octanoylamino-[1,3,2]dioxasilinan-2-yl)-propyl ester, octanethioic acid 3-(5-ethyl-2-{2-ethyl-4-hexyloxycarbonyloxy-2-hexyloxycarbonyloxymethyl-3-[2-(3-octanoylsulfanyl-propyl)-[1,3,2]dioxasilinan-2-yloxy]-butoxy}-5-hexyloxycarbonyloxymethyl-[1,3,2]dioxasilinan-2-yl)-propyl ester, octanethioic acid 3-(5-ethyl-2-{2-ethyl-4-hexylcarbamoyloxy-2-hexylcarbamoyloxymethyl-3-[2-(3-octanoylsulfanyl-propyl)-[1,3,2]dioxasilinan-2-yloxy]-butoxy}-5-hexylcarbamoyloxymethyl-[1,3,2]dioxasilinan-2-yl)-propyl ester, octanethioic acid 3-(5-ethyl-2-{2-ethyl-4-hexylcarbamoyloxy-2-hexylcarbamoyloxymethyl-3-[2-(3-mercapto-propyl)-[1,3,2]dioxasilinan-2-yloxy]-butoxy}-5-hexylcarbamoyloxymethyl-[1,3,2]dioxasilinan-2-yl)-propyl ester, acetic acid 2-[ethoxy-(4-mercapto-butyl)-methyl-silanyloxymethyl]-2-[ethoxy-(3-mercapto-propyl)-methyl-silanyloxymethyl]-butyl ester, N-{2-[ethoxy-(4-mercapto-butyl)-methyl-silanyloxymethyl]-2-[ethoxy-(3-mercapto-propyl)-methyl-silanyloxymethyl]-butyl}-acetamide, carbonic acid 2-[ethoxy-(4-mercapto-butyl)-methyl-silanyloxymethyl]-2-[ethoxy-(3-mercapto-propyl)-methyl-silanyloxymethyl]-butyl ester propyl ester, thioacetic acid S-[3-(ethoxy-{2-[ethoxy-(4-mercapto-butyl)-methyl-silanyloxymethyl]-2-propoxycarbonyloxymethyl-butoxy}-methyl-silanyl)-propyl]ester, thioacetic acid S-[3-(ethoxy-{2-[ethoxy-(4-mercapto-butyl)-ethoxy-silanyloxymethyl]-2-propoxycarbonyloxymethyl-butoxy}-ethoxy-silanyl)-propyl]ester, acetic acid 2-{2-acetoxymethyl-2-[{2-acetoxymethyl-2-[ethoxy-(3-mercapto-propyl)-methyl-silanyloxymethyl]-butoxy}-(3-acetylsulfanyl-propyl)-methyl-silanyloxymethyl]-butoxy}-5-ethyl-2-(3-mercapto-propyl)-[1,3,2]dioxasilinan-5-ylmethyl ester, octanoic acid 2-{2-octanoyloxymethyl-2-[{2-octanoyloxymethyl-2-[ethoxy-(3-mercapto-propyl)-methyl-silanyloxymethyl]-butoxy}-(3-octanonylsulfanyl-propyl)-methyl-silanyloxymethyl]-butoxy}-5-ethyl-2-(3-mercapto-propyl)-[1,3,2]dioxasilinan-5-ylmethyl ester, acetic acid 2-[{2-acetoxymethyl-2-[ethoxy-(3-mercapto-propyl)-ethoxy-silanyloxymethyl]-butoxy}-(3-acetylsulfanyl-propyl)-ethoxy-silanyloxymethyl]-2-[ethoxy-(3-mercapto-propyl)-methyl-silanyloxymethyl]-butyl ester, acetic acid 2-[{2-acetoxymethyl-2-[ethoxy-(3-mercapto-propyl)-methyl-silanyloxymethyl]-butoxy}-(3-acetylsulfanyl-propyl)-methyl-silanyloxymethyl]-2-[(3-acetylsulfanyl-propyl)-ethoxy-methyl-silanyloxymethyl]-butyl ester, octanoic acid 2-[{2-octanoyloxymethyl-2-[ethoxy-(3-mercapto-propyl)-ethoxy-silanyloxymethyl]-butoxy}-(3-octanoylsulfanyl-propyl)-methyl-silanyloxymethyl]-2-[(3-octanoylsulfanyl-propyl)-diethoxy-silanyloxymethyl]-butyl ester, acetic acid 2,2-bis-[(3-acetylsulfanyl-propyl)-(2,2-bis-hydroxymethyl-butoxy)-methyl-silanyloxymethyl]-butyl ester, acetic acid 2,2-bis-[(3-acetylsulfanyl-propyl)-(2,2-bis-hydroxymethyl-butoxy)-ethoxy-silanyloxymethyl]-butyl ester, octanoic acid 2-[(3-octanoylsulfanyl-propyl)-(2,2-bis-hydroxymethyl-butoxy)-ethyl-silanyloxymethyl]-2-[(2,2-bis-hydroxymethyl-butoxy)-(3-mercapto-propyl)-methyl-silanyloxymethyl]-butyl ester, octanoic acid 2-[(3-octanoylsulfanyl-propyl)-ethoxy-(2,2-bis-hydroxymethyl-butoxy)-silanyloxymethyl]-2-[(2,2-bis-hydroxymethyl-butoxy)-(3-mercapto-propyl)-ethoxy-silanyloxymethyl]-butyl ester, and octanoic acid 2-[ethoxymethyl-(2,2-bis-octanoyloxymethyl-butoxy)-(3-octanonylsulfanyl-propyl)-silanyloxymethyl]-2-[(2,2-bis-aoctanoyloxymethyl-butoxy)-(3-mercapto-propyl)-ethoxy-silanyloxymethyl]-butyl ester.

9. The partial to substantially complete hydrolyzate(s) of sulfur-containing silane of general Formula (1) of claim 1.

10. A process for preparing sulfur-containing silane prepared by the process which comprises reacting
a) at least one sulfur-containing silane of general Formulae (2), (3), (4), (5) and (6):

$$(Y^1S)\text{-}G^1\text{-}(SiX^1X^2X^3) \quad (2)$$

$$(Y^2S)\text{-}G^2\text{-}(SiX^1X^2X^3) \quad (3)$$

$$(Y^3S)\text{-}G^3\text{-}(SiX^1X^2X^3) \quad (4)$$

$$(Y^4S)\text{-}G^4\text{-}(SiX^1X^2X^3) \quad (5)$$

$$(Y^5S)\text{-}G^5\text{-}(SiX^1X^2X^3) \quad (6)$$

wherein:
each occurrence of $G^1$, $G^2$, $G^3$, $G^4$ and $G^5$ is independently a hydrocarbylene group containing from 1 to 15 carbon atoms selected from the group consisting of alkylene, alkenylene, arylene, or aralkylene;
each occurrence of $X^1$ is independently selected from the group consisting of —Cl, —Br, $R^3O$—, $R^3C(=O)O$—, $R^3{}_2C=NO$—, and $R^3{}_2NO$—, wherein each $R^3$ is independently selected from the group consisting of hydrogen and straight, cyclic or branched alkyl, alkenyl, aryl, and aralkyl groups containing up to 30 carbon atoms;
each occurrence of $X^2$ and $X^3$ is independently selected from the group consisting of —Cl, —Br, $R^3O$—, $R^3C(=O)O$—, $R^3{}_2C=NO$—, $R^3{}_2NO$— and R, wherein each occurrence of R is independently selected from the group consisting of straight, cyclic or branched alkyl, alkenyl, aryl, and aralkyl groups containing from 1 to 12 carbon atoms, and each occurrence of $R^3$ is independently selected from the group consisting of hydrogen and straight, cyclic and branched alkyl, alkenyl, aryl, and aralkyl groups containing up to 30 carbon atoms;
each occurrence of $Y^1$, $Y^2$, $Y^3$, $Y^3$, and $Y^5$ is independently selected from the group consisting of hydrogen and an acyl group, $R^3C(=O)$—, wherein each occurrence of $R^3$ is independently selected from the group consisting of hydrogen, straight, cyclic and branched alkyl, alkenyl, aryl, and aralkyl groups containing up to 30 carbon atoms; with
b) one or more dihydroxyl-containing compounds of general Formula (7):

$$R^1A^1C(=O)A^2G^6(OH)_2, \quad (7)$$

wherein $A^1$ is selected from the group consisting of a covalent chemical bond between $R^1$ and the carbonyl group, an oxygen atom and —$NR^2$—; $A^2$ is selected from the group consisting of a covalent chemical bond between $G^6$ and the carbonyl group, oxygen atom and —$NR^2$—; $R^1$ is selected from the group consisting of hydrogen and straight, cyclic and branched alkyl, alkenyl, aryl, and aralkyl groups containing up to 18 carbon atoms; $R^2$ is independently selected from the group consisting of hydrogen and straight, cyclic or branched alkyl, alkenyl, aryl, and aralkyl groups containing up to 18 carbon atoms; and, $G^6$ is a hydrocarbylene group of from 3 to 15 carbon atoms; thereby producing sulfur-containing silane of Formula (1).

11. The process of claim 10 wherein the sulfur-containing silane(s) of Formulae (2) to (6) are further reacted with one or more monohydroxyl-containing compounds of general Formula (8):

$$[R^1A^1C(=O)A^2]_2G^6OH, \quad (8)$$

wherein each occurrence of $A^1$ is independently selected from the group consisting of a covalent chemical bond between $R^1$ and the carbonyl group, oxygen atom and —$NR^2$—; each occurrence of $A^2$ is independently selected from the group consisting of a covalent chemical bond between $G^6$ and the carbonyl group, an oxygen atom and —$NR^2$—; each occurrence of $R^1$ is independently selected from the group consisting of hydrogen and straight, cyclic or branched alkyl, alkenyl, aryl, and aralkyl groups containing up to 18 carbon atoms; each occurrence of $R^2$ is independently selected from the group consisting of hydrogen and straight, cyclic or branched alkyl, alkenyl, aryl, and aralkyl groups containing up to 18 carbon atoms; and, $G^6$ is a hydrocarbylene group of from 3 to 15 carbon atoms.

12. The process of claim 10 wherein the sulfur-containing silane(s) of Formulae (2) to (6) are further reacted with one or more dihydroxyl- and/or trihydroxyl-containing compounds of general Formula (9):

$$H\text{-}A^2G^6(OH)_2 \quad (9)$$

wherein $A^2$ is selected from the group consisting of an oxygen atom and —$NR^2$— wherein $R^2$ is selected from the group consisting of hydrogen and straight, cyclic and branched alkyl, akenyl, aryl, and aralkyl groups containing up to 10 carbon atoms; and, $G^6$ is independently a hydrocarbylene group of from 3 to 15 carbon atoms.

13. The process of claim 10 wherein the process is carried out in a continuous operation which comprises:
a) reacting, in a thin film reactor, a thin film reaction medium comprising a mixture of at least one silane of Formulae (2), (3), (4) (5) and/or (6) with at least one polyhydroxy-containing compound of Formula (7), optionally of Formulae (8) and/or (9), and optionally a transesterification catalyst, to provide silane(s) that contain a cyclic and/or bridged dialkoxy group, and by-product monoalcohol;
b) vaporizing by-product monoalcohol from the thin film to drive the reaction;
c) optionally, recovering by-product monoalcohol;
d) recovering reaction product(s); and,
e) optionally, neutralizing the reaction medium to increase the storage stability of the silane product(s) therein.

14. The process of claim 10 wherein the reaction is carried out at a temperature ranging from 0 to 200° C. while maintaining a pressure in the range of from 0.1 to 2000 mm Hg absolute.

15. The process of claim 10 carried out in the presence of a catalytically effective amount of at least one transesterification catalysts.

16. The process of claim 10 wherein the process provides at least one sulfur-containing silane product selected from the group consisting of hexanoic acid 2-(3-butyrylsulfanyl-propyl)-5-ethyl-2-methyl-[1,3,2]dioxasilinan-5-yl ester, hexanoic acid 2-(3-butyrylsulfanyl-propyl)-5-ethyl-2-ethoxy-[1,3,2]dioxasilinan-5-yl ester, hexanoic acid 2-(3-butyrylsulfanyl-propyl)-2-(3-hexanoyloxy-4-hydroxy-propoxy)-[1,3,2]dioxasilinan-5-yl ester, octanoic acid 2-(3-hexanoyloxymethyl-4-hydroxy-3-methyl-propoxy)-2-(3-hexanoylsulfanyl-propyl)-5-methyl-[1,3,2]dioxasilinan-5-ylmethyl ester, octanoic acid 2-(3-hexanoyloxymethyl-4-hydroxy-3-methyl-propoxy)-2-(3-mercapto-propyl)-5-methyl-[1,3,2]dioxasilinan-5-ylmethyl ester, 2-ethyl-hexanoic acid 2-[3-(2-ethyl-hexanoyloxymethyl)-4-hydroxy-3 -methyl-propoxy]-2-[3-(2-ethyl-hexanoylsulfanyl)-propyl]-5-methyl-[1,3,2]dioxasilinan-5-ylmethyl ester, 2-ethyl-hexanoic acid 2-[4-(2-ethyl-hexanoyloxy)-3-methyl-butoxy]-2-[3-(2-ethyl-hexanoylsulfanyl)-propyl]-5-methyl-[1,3,2]dioxasilinan-5-ylmethyl ester, octanoic acid 5-ethyl-2-(3-mercapto-propyl)-2-methyl-[1,3,2]dioxasilinan-5-yl ester, octanoic acid 2-ethoxy-5-ethyl-2-(3-mercapto-propyl)-[1,3,2]dioxasilinan-5-yl ester,octanoic acid 2-(2,2-bis-hydroxymethyl-butoxy)-5-ethyl-2-(3-mercapto-propyl)-[1,3,2]dioxasilinan-5-yl ester, octanoic acid 5-ethyl-2-(2-hydroxymethyl-2-octanoyloxymethyl-butoxy)-2-(3-mercapto-propyl)-[1,3,2] dioxasilinan-5-yl ester, octanoic acid 2-(2,2-bis-octanoyloxymethyl-butoxy)-5-ethyl-2-(3-mercapto-propyl)-[1,3,2]dioxasilinan-5-yl ester, octanoic acid 2-(2,2-bis-octanoyloxymethyl-butoxy)-5-ethyl-2-(3-octanoylsulfanyl-propyl)-[1,3,2]dioxasilinan-5-yl ester, octanoic acid 5-ethyl-2-(2-hydroxymethyl-2-octanoyloxymethyl-butoxy)-2-(3-octanoylsulfanyl-propyl)-[1,3,2]dioxasilinan-5-yl ester, octanoic acid 5-ethyl-2-{2-[5-ethyl-5-hydroxymethyl-2-(3-mercapto-propyl)-[1,3,2]dioxasilinan-2-yloxymethyl]-2-octanoyloxymethyl-butoxy}-2-(3-octanoylsulfanyl-propyl)-[1,3,2]dioxasilinan-5-yl ester, octanoic acid 5-ethyl-2-{2-[5-ethyl-5-octanoyloxymethyl-2-(3-octanoylsulfanyl-propyl)-[1,3,2]dioxasilinan-2-yloxymethyl]-2-octanoyloxymethyl-butoxy}-2-(3-octanoylsulfanyl-propyl)-[1,3,2]dioxasilinan-5-yl ester, octanethioic acid 3-(5-ethyl-2-{2-ethyl-4-(3-ethyl-3-methyl-heptanoylamino)-2-(octanoylamino-methyl)-3-[2-(3-octanoylsulfanyl-propyl)-[1,3,2]dioxasilinan-2-yloxy]-butoxy}-5-octanoylamino-[1,3,2]dioxasilinan-2-yl)-propyl ester, octanethioic acid 3-(5-ethyl-2-{2-ethyl-4-hexyloxycarbonyloxy-2-hexyloxycarbonyloxymethyl-3-[2-(3-octanoylsulfanyl-propyl)-[1,3,2]dioxasilinan-2-yloxy]-butoxy}-5-hexyloxycarbonyloxymethyl-[1,3,2]dioxasilinan-2-yl)-propyl ester, octanethioic acid 3-(5-ethyl-2-{2-ethyl-4-hexylcarbarnoyloxy-2-hexylcarbamoyloxymethyl-3-[2-(3-octanoylsulfanyl-propyl)-[1,3,2]dioxasilinan-2-yloxy]-butoxy}-5-hexylcarbamoyloxymethyl-[1,3,2]dioxasilinan-2-yl)-propyl ester, octanethioic acid 3-(5-ethyl-2-{2-ethyl-4-hexylcarbamoyloxy-2-hexylcarbamoyloxymethyl-3-[2-(3-mercapto-propyl)-[1,3,2]dioxasilinan-2-yloxy-butoxy}-5-hexylcarbamoyloxymethyl-[1,3,2]dioxasilinan-2-yl)-propyl ester, acetic acid 2-[ethoxy-(4-mercapto-butyl)-methyl-silanyloxymethyl]-2-[ethoxy-(3-mercapto-propyl)-methyl-silanyloxymethyl]-butyl ester, N-{2-[ethoxy-(4-mercapto-butyl)-methyl-silanyloxymethyl]-2-[ethoxy-(3-mercapto-propyl)-methyl-silanyloxymethyl]-butyl}-acetamide, carbonic acid 2-[ethoxy-(4-mercapto-butyl)-methyl-silanyloxymethyl]-2-[ethoxy-(3 -mercapto-propyl)-methyl-silanyloxymethyl]-butyl ester propyl ester, thioacetic acid S-[3-(ethoxy-{2-[ethoxy-(4-mercapto-butyl)-methyl-silanyloxymethyl]-2-propoxycarbonyloxymethyl-butoxy}-methyl-silanyl)-propyl]ester, thioacetic acid S-[3-(ethoxy-{2-[ethoxy-(4-mercapto-butyl)-ethoxy-silanyloxymethyl]-2-propoxycarbonyloxymethyl-butoxy}-ethoxy-silanyl)-propyl]ester, acetic acid 2-{2-acetoxymethyl-2-[{2-acetoxymethyl-2-[ethoxy-(3-mercapto-propyl)-methyl-silanyloxymethyl]-butoxy}-(3-acetylsulfanyl-propyl)-methyl-silanyloxymethyl]-butoxy}-5-ethyl-2-(3-mercapto-propyl)-[1,3,2]dioxasilinan-5-ylmethyl ester, octanoic acid 2-{2-octanoyloxymethyl-2-[{2-octanoyloxymethyl-2-[ethoxy-(3-mercapto-propyl)-methyl-silanyloxymethyl]-butoxy}-(3-octanonylsulfanyl-propyl)-methyl-silanyloxymethyl]-butoxy}-5-ethyl-2-(3-mercapto-propyl)-[1,3,2]dioxasilinan-5-ylmethyl ester, acetic acid 2-[{2-acetoxymethyl-2-[ethoxy-(3-mercapto-propyl)-ethoxy-silanyloxymethyl]-butoxy}-(3-acetylsulfanyl-propyl)-ethoxy-silanyloxymethyl]-2-[ethoxy-(3-mercapto-propyl)-methyl-silanyloxymethyl]-butyl ester, acetic acid 2-[{2-acetoxymethyl-2-[ethoxy-(3-mercapto-propyl)-methyl-silanyloxymethyl]-butoxy}-(3-acetylsulfanyl-propyl)-methyl-silanyloxymethyl]-2-[(3-acetylsulfanyl-propyl)-ethoxy-methyl-silanyloxymethyl]-butyl ester, octanoic acid 2-[{2-octanoyloxymethyl-2-[ethoxy-(3-mercapto-propyl)-ethoxy-silanyloxymethyl]-butoxy}-(3-octanoylsulfanyl-propyl)-methyl-silanyloxymethyl]-2-[(3-octanoylsulfanyl-propyl)-diethoxy-silanyloxymethyl]-butyl ester, acetic acid 2,2-bis-[(3-acetylsulfanyl-propyl)-(2,2-bis-hydroxymethyl-butoxy)-methyl-silanyloxymethyl]-butyl ester, acetic acid 2,2-bis-[(3-acetylsulfanyl-propyl)-(2,2-bis-hydroxymethyl-butoxy)-ethoxy-silanyloxymethyl]-butyl ester, octanoic acid 2-[(3-octanoylsulfanyl-propyl)-(2,2-bis-hydroxymethyl-butoxy)-ethyl-silanyloxymethyl]-2-[(2,2-bis-hydroxymethyl-butoxy)-(3-mercapto-propyl)-methyl-silanyloxymethyl]-butyl ester, octanoic acid 2-[(3-octanoylsulfanyl-propyl)-ethoxy-(2,2-bis-hydroxymethyl-butoxy)-silanyloxymethyl]-2-[(2,2-bis-hydroxymethyl-butoxy)-(3-mercapto-propyl)-ethoxy-silanyloxymethyl]-butyl ester, and octanoic acid 2-[ethoxymethyl-(2,2-bis-octanoyloxymethyl-butoxy)-(3-octanonylsulfanyl-propyl)-silanyloxymethyl]-2-[(2,2-bis-aoctanoyloxymethyl-butoxy)-(3-mercapto-propyl)-ethoxy-silanyloxymethyl]-butyl ester.

17. Free-flowing particulate composition which comprises:
   a) at least one particulate filler; and,
   b) at least one silane of Formula (1) in admixture with and/or chemically bonded to particulate (a).

18. The free-flowing particulate composition of claim 17 wherein the particulate is at least one member selected from the group consisting of metal oxide, siliceous material and carbon black.

19. The free-flowing particulate composition of claim 18 wherein the metal oxide is at least one member selected from the group consisting of silica, titanium and alumina; and, the siliceous material is at least one member of the group consisting of aluminosilicate, clay and talc.

20. The free-flowing particulate composition of claim 19 wherein the particulate is at least one member selected from the group consisting of mixtures of silica and carbon black and mixtures of silica and alumina.

21. A rubber composition comprising (a) at least one rubber component, (b) at least one particulate filler and (c) at least one sulfur-containing silane of claim 1.

22. An article of manufacture selected from the group consisting of tires, industrial goods, shoe soles, hoses, seals, gaskets and cable jackets of which at least one component is the cured rubber composition of claim 21.

* * * * *